United States Patent
Scott et al.

(10) Patent No.: US 12,324,583 B2
(45) Date of Patent: Jun. 10, 2025

(54) INCOMPATIBLE STAPLE CARTRIDGE USE PREVENTION FEATURES FOR SURGICAL STAPLER

(71) Applicant: Cilag GmbH International, Zug (CH)

(72) Inventors: Gregory G Scott, Cincinnati, OH (US); Nicholas Fanelli, Morrow, OH (US); Richard L. Leimbach, Cincinnati, OH (US); John P. May, Mason, OH (US); Kevin M. Fiebig, Cincinnati, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/588,094

(22) Filed: Feb. 27, 2024

(65) Prior Publication Data
US 2024/0382201 A1 Nov. 21, 2024

Related U.S. Application Data

(60) Provisional application No. 63/467,615, filed on May 19, 2023.

(51) Int. Cl.
*A61B 17/072* (2006.01)
(52) U.S. Cl.
CPC .............. *A61B 17/07207* (2013.01); *A61B 2017/07271* (2013.01)
(58) Field of Classification Search
CPC ............................................ A61B 17/07207
See application file for complete search history.

(56) References Cited

U.S. PATENT DOCUMENTS

| | | | |
|---|---|---|---|
| 6,988,649 B2 | 1/2006 | Shelton, IV et al. |
| 7,380,696 B2 | 6/2008 | Shelton, IV et al. |
| 8,453,914 B2 | 6/2013 | Laurent et al. |
| 9,186,142 B2 | 11/2015 | Fanelli et al. |
| 9,717,497 B2 | 8/2017 | Zerkle et al. |
| 9,808,248 B2 | 11/2017 | Hoffman |

(Continued)

FOREIGN PATENT DOCUMENTS

EP 3545858 A1 10/2019

OTHER PUBLICATIONS

Partial International Search Report and Written Opinion dated Sep. 11, 2024, for International Application No. PCT/IB2024/054889, 15 pages.

(Continued)

*Primary Examiner* — Nathaniel C Chukwurah
(74) *Attorney, Agent, or Firm* — Frost Brown Todd LLC

(57) ABSTRACT

A surgical stapler kit includes a surgical stapler having a body, a shaft, and an end effector. The kit includes a first staple cartridge having a first cartridge body and a first sled, and a second staple cartridge having a second cartridge body and a second sled. When the first staple cartridge is at least partially seated within a cartridge jaw with the first sled in a proximal undisplaced position, a knife drives the first sled distally to deploy staples from the first cartridge body. When the second staple cartridge is at least partially seated within the cartridge jaw with the second sled in a proximal undisplaced position, the knife advances distally into a lockout position before causing any staples to be deployed from the second cartridge body.

20 Claims, 23 Drawing Sheets

(56) References Cited

U.S. PATENT DOCUMENTS

| | | | |
|---|---|---|---|
| 9,839,421 | B2 | 12/2017 | Zerkle et al. |
| 10,092,292 | B2 | 10/2018 | Boudreaux et al. |
| 10,130,359 | B2 | 11/2018 | Hess et al. |
| 10,335,147 | B2 | 7/2019 | Rector et al. |
| 11,278,288 | B2 * | 3/2022 | Rector ............. A61B 17/07207 |
| 11,406,379 | B2 | 8/2022 | Hess et al. |
| 11,540,826 | B2 | 1/2023 | Nalagatla et al. |
| 2015/0374373 | A1 | 12/2015 | Rector et al. |
| 2022/0370069 | A1 | 11/2022 | Simms et al. |
| 2023/0051222 | A1 | 2/2023 | Shelton, IV et al. |

OTHER PUBLICATIONS

International Search Report and Written Opinion dated Nov. 4, 2024, for International Application No. PCT/IB2024/054889, 21 pages.
U.S. Appl. No. 18/588,147.
U.S. Appl. No. 18/588,175.
U.S. Appl. No. 18/588,206.
U.S. Appl. No. 18/588,240.
U.S. Appl. No. 18/588,269.
U.S. Appl. No. 18/588,684.
U.S. Appl. No. 18/758,887.
U.S. Appl. No. 18/588,147, entitled "Surgical Stapler Cartridge Having Intermediate Raised Tissue Engagement Protrusions," filed Feb. 27, 2024.
U.S. Appl. No. 18/588,175, entitled "Surgical Stapler Cartridge Having Tissue Engagement Protrusions with Enlarged Engagement Surface," filed Feb. 27, 2024.
U.S. Appl. No. 18/588,206, entitled "Surgical Stapler Cartridge Having Raised Surface to Promote Buttress Adhesion," filed Feb. 27, 2024.
U.S. Appl. No. 18/588,240, entitled "Surgical Stapler Cartridge Having Cartridge Retention Features," filed Feb. 27, 2024.
U.S. Appl. No. 18/588,269, entitled "Surgical Stapler Anvil Having Staple Forming Pockets with Laterally Varying Orientations," filed Feb. 27, 2024.
U.S. Appl. No. 18/588,684, entitled "Method of Surgical Stapling," filed Feb. 27, 2024.
U.S. Appl. No. 18/758,887, entitled "Sled Retention and Alignment Features for Surgical Stapler," filed Jun. 28, 2024.

* cited by examiner

INCOMPATIBLE STAPLE CARTRIDGE USE PREVENTION FEATURES FOR SURGICAL STAPLER

PRIORITY

This application claims the benefit of U.S. Provisional Pat. App. No. 63/467,615, entitled "Incompatible Staple Cartridge Use Prevention Features for Surgical Stapler," filed May 19, 2023, the disclosure of which is incorporated by reference herein in its entirety.

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In a surgical procedure setting in which multiple different types of surgical staplers and/or multiple different types of staple cartridges are made available to a clinician for use in the procedure, a theoretical scenario could arise in which the clinician inadvertently selects a staple cartridge that is not designed for use with the particular surgical stapler selected by the clinician. In other words, the staple cartridge selected by the clinician could be incompatible with the surgical stapler. Nevertheless, the incompatible staple cartridge could be structurally similar enough to a compatible staple cartridge (i.e., one designed specifically for use with the selected surgical stapler) that the incompatible staple cartridge is capable of being at least partially seated within the cartridge jaw of the surgical stapler by the clinician. Additionally, the end effector of the surgical stapler may be capable of at least partially closing with the incompatible staple cartridge loaded, which could result in the clinician mistakenly believing that the end effector is properly loaded and ready for firing on patient tissue. Furthermore, if the incompatible staple cartridge has not previously been fired (or "spent"), the surgical stapler could be capable of at least partially firing the incompatible staple cartridge in response to the clinician's input. The incompatibility of the staple cartridge with the surgical stapler could result in the staples ejected by the incompatible staple cartridge being improperly formed by surgical stapler's anvil jaw, and thus being ineffective to properly seal the patient tissue being fired upon.

The surgical stapling features of the present disclosure seek to protect against inadvertent clinician misuse by inhibiting loading of an incompatible staple cartridge into a selected surgical stapler, and subsequent firing of the incompatible staple cartridge with the surgical stapler. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

Figure 1:
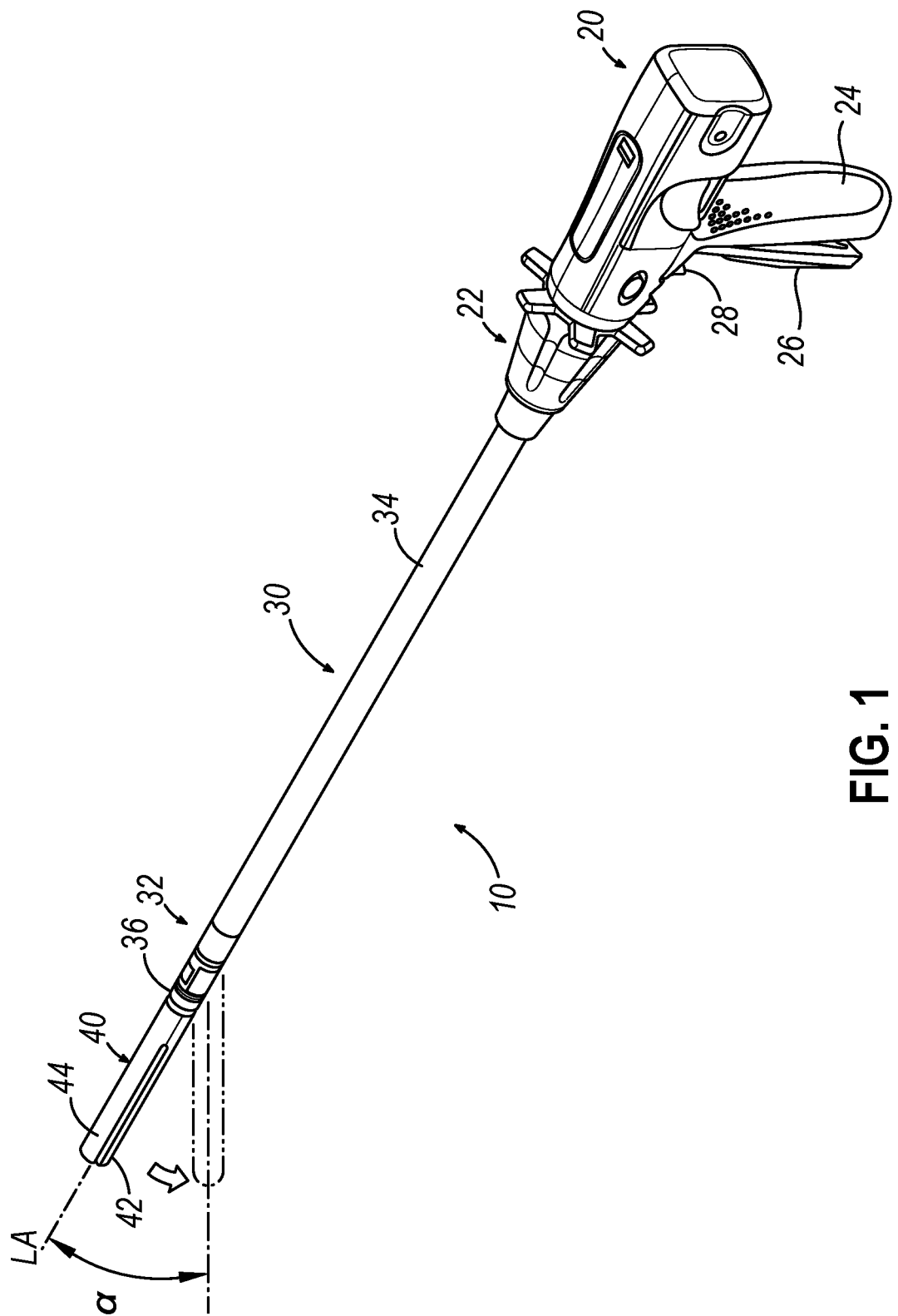
FIG. 1 depicts a perspective view of an example of a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures, and "substantially equal" values encompass nominally equal values.

I. Illustrative Surgical Stapler

A. Overview of Surgical Stapler Features

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (LA) and distally terminates at an articulation joint (32), and an end effector (40) operatively coupled with shaft (30) via articulation joint (32).

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (LA) at a desired angle (a). Articulation joint (32) and related features for manipulating articulation joint (32) may be further configured in accordance with the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a "reload"), and an upper jaw exemplified as an anvil jaw (44)) (also referred to as an "anvil") that pivots relative to cartridge jaw (42) to clamp tissue therebetween. In other versions, end effector (40) may be alternatively configured such that cartridge jaw (42) pivots relative to anvil jaw (44). Unless otherwise described, the term "pivot" (and variations thereof) as used herein in connection with the relative motion between jaws (42, 44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term "pivot" and variations thereof as used herein with reference to the relative motion between jaws (42, 44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member (also referred to as a firing driver) exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 2:
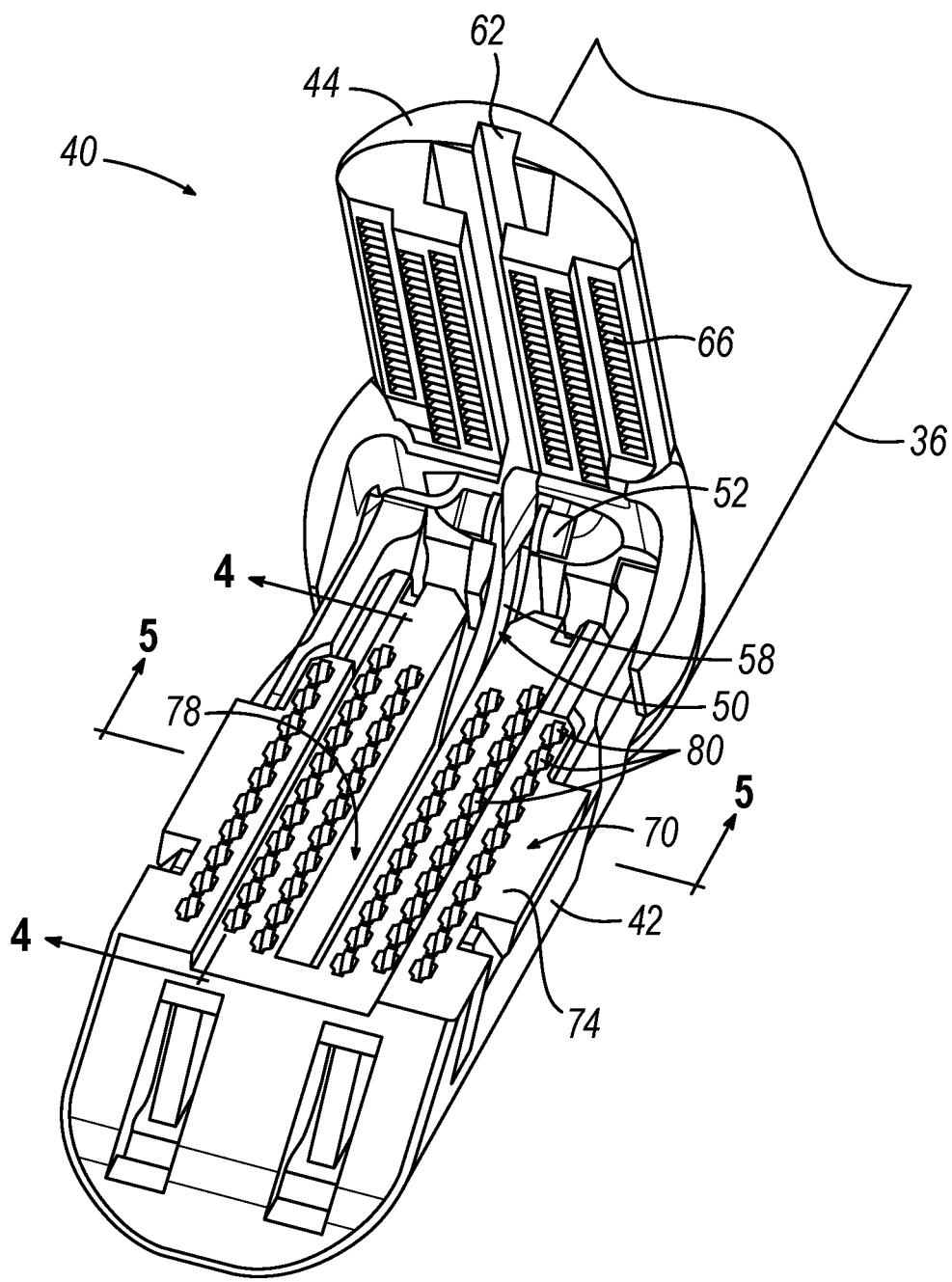
FIG. 2 depicts a perspective view of an end effector of the surgical stapler of FIG. 1, shown in an open state.
Figure 3:
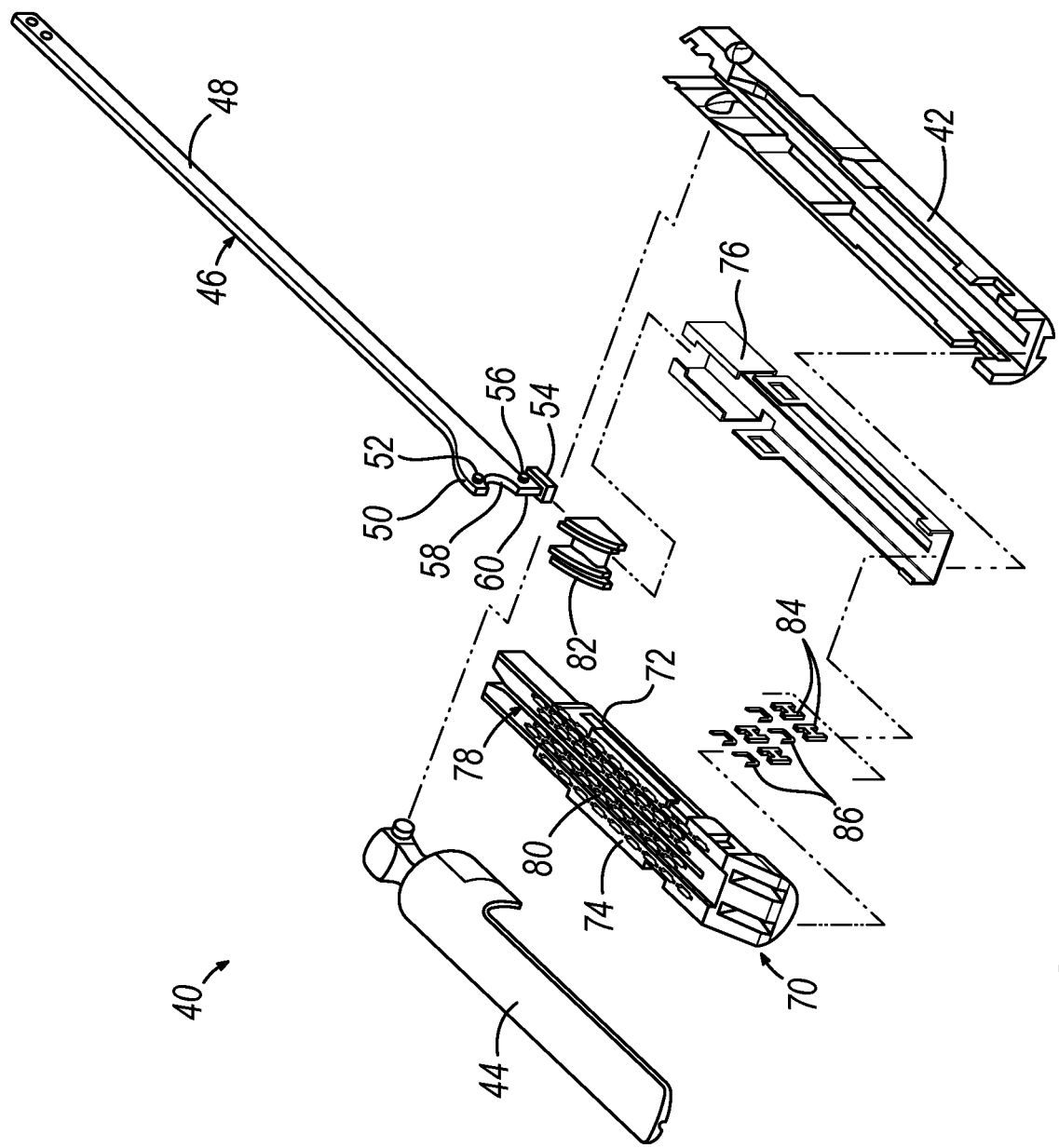
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably seated within a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body (72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
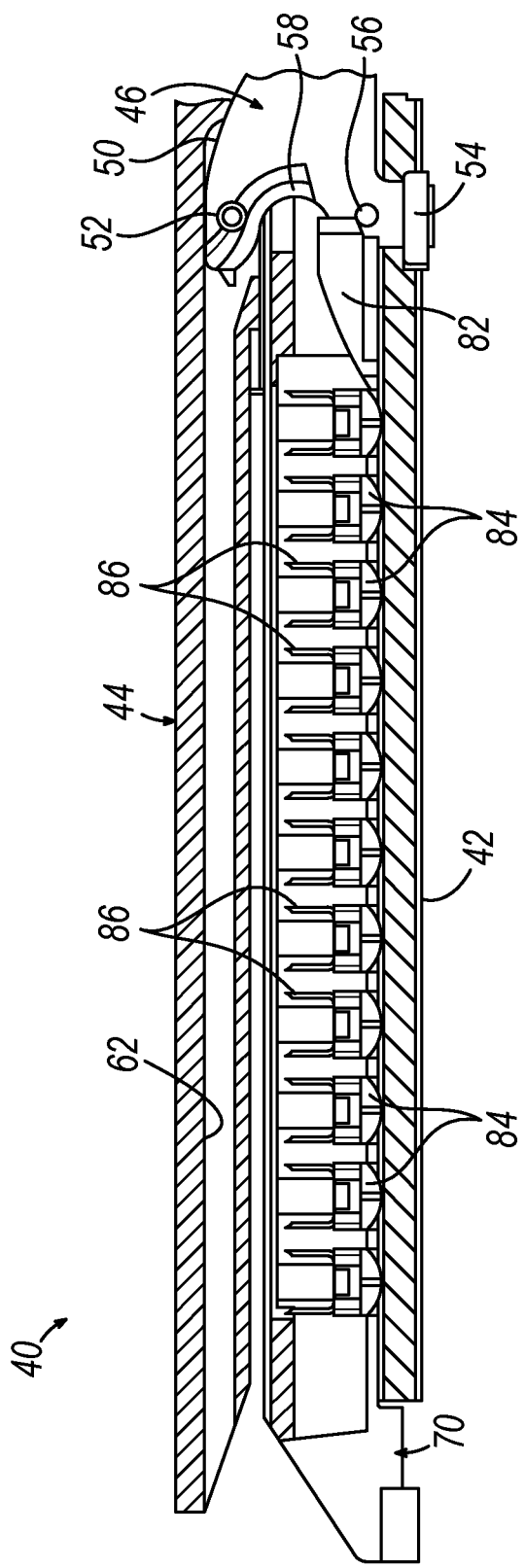
FIG. 4A depicts a side cross-sectional view of the end effector of FIG. 2, taken along line 4-4 of FIG. 2, showing a firing beam and sled in a proximal undisplaced position.
Figure 4B:
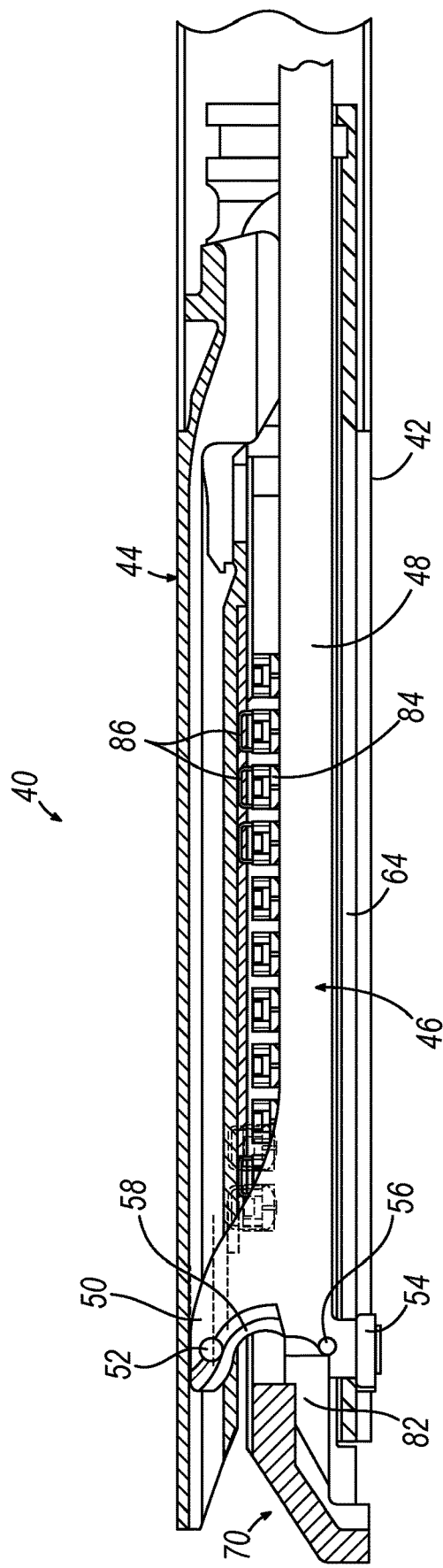
FIG. 4B depicts a side cross-sectional view of the end effector of FIG. 2, taken along line 4-4 of FIG. 2, showing the firing beam and sled in a distal fired position.
Figure 5:
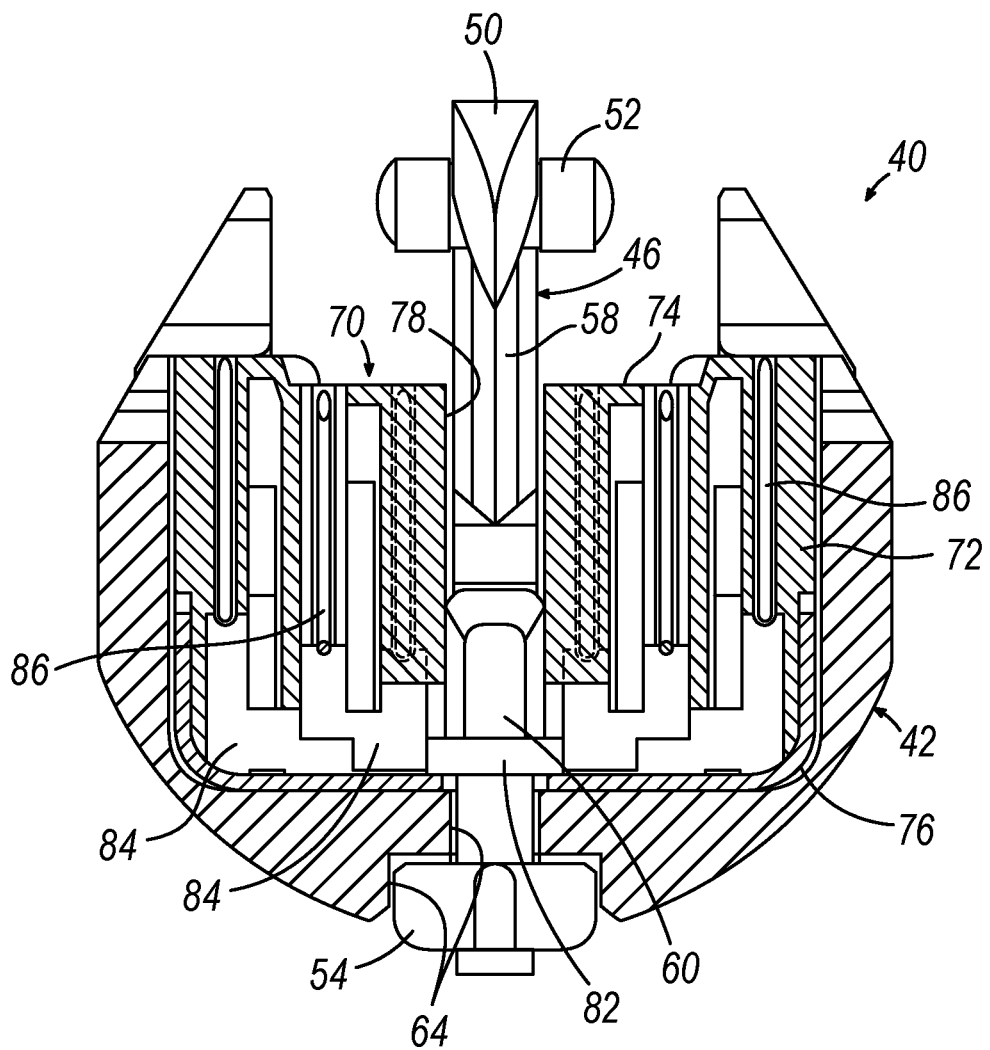
FIG. 5 depicts an end cross-sectional view of the end effector of FIG. 2, taken along line 5-5 of FIG. 2 and omitting an upper anvil jaw, showing further details of a distal knife portion of the firing beam and the sled.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (43) is aligned with and movable vertically within a respective cartridge pocket (51). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,A248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
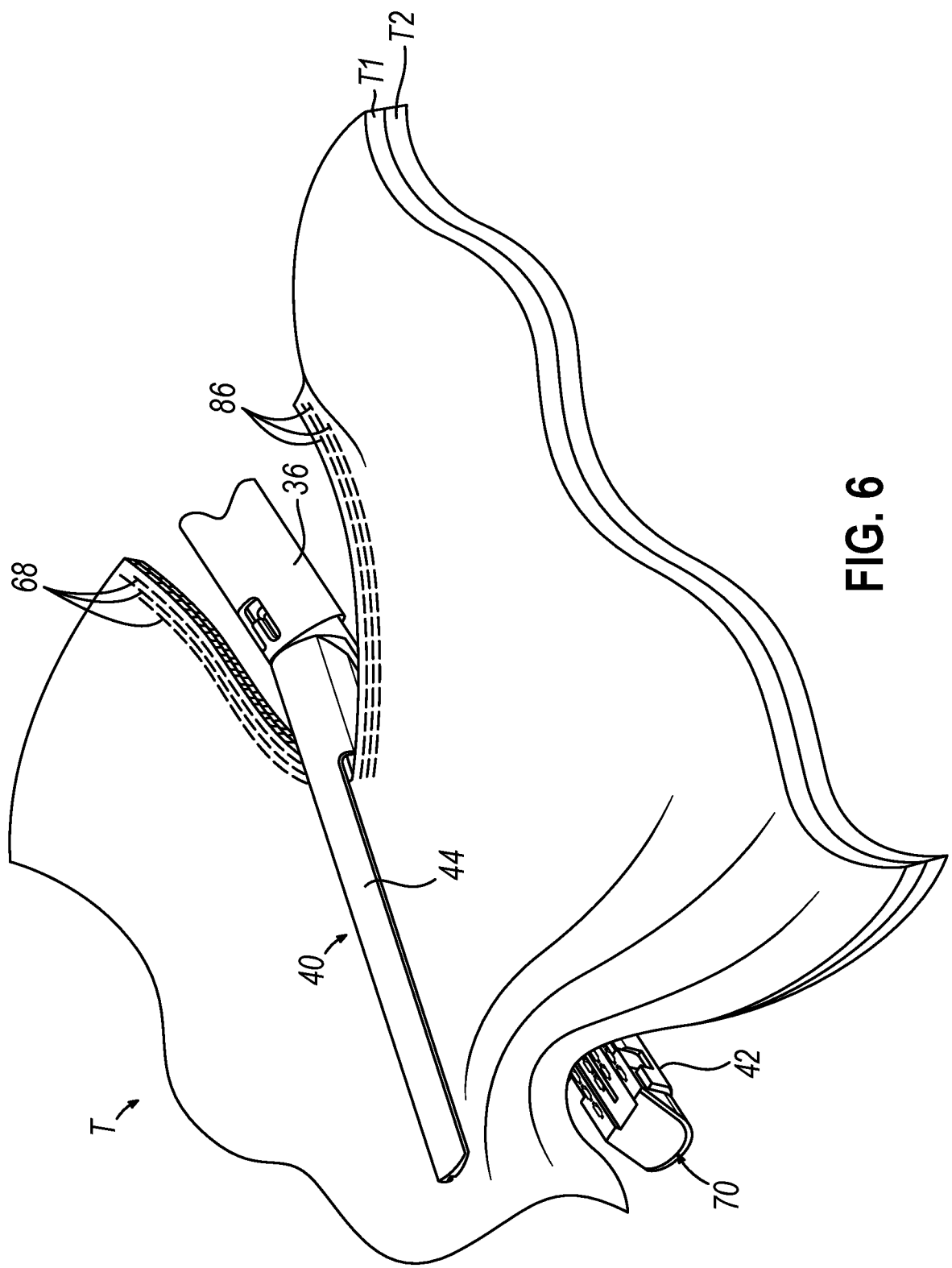
FIG. 6 depicts a perspective view of the end effector of FIG. 3, shown after having been fired once on a first section of tissue and being positioned to clamp and fire on a second section of tissue.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

B. Illustrative End Effector Firing Lockout Features

In some instances, it may be desirable to provide a firing lockout feature for end effector (40) to prevent clamped tissue from being severed without being stapled. In particular, it may be desirable to prevent sled (82) and cutting edge (58) from advancing distally if staple cartridge (70) is spent (i.e., has already been fired), or if a staple cartridge (70) is entirely absent from cartridge jaw (42).

Figure 7:
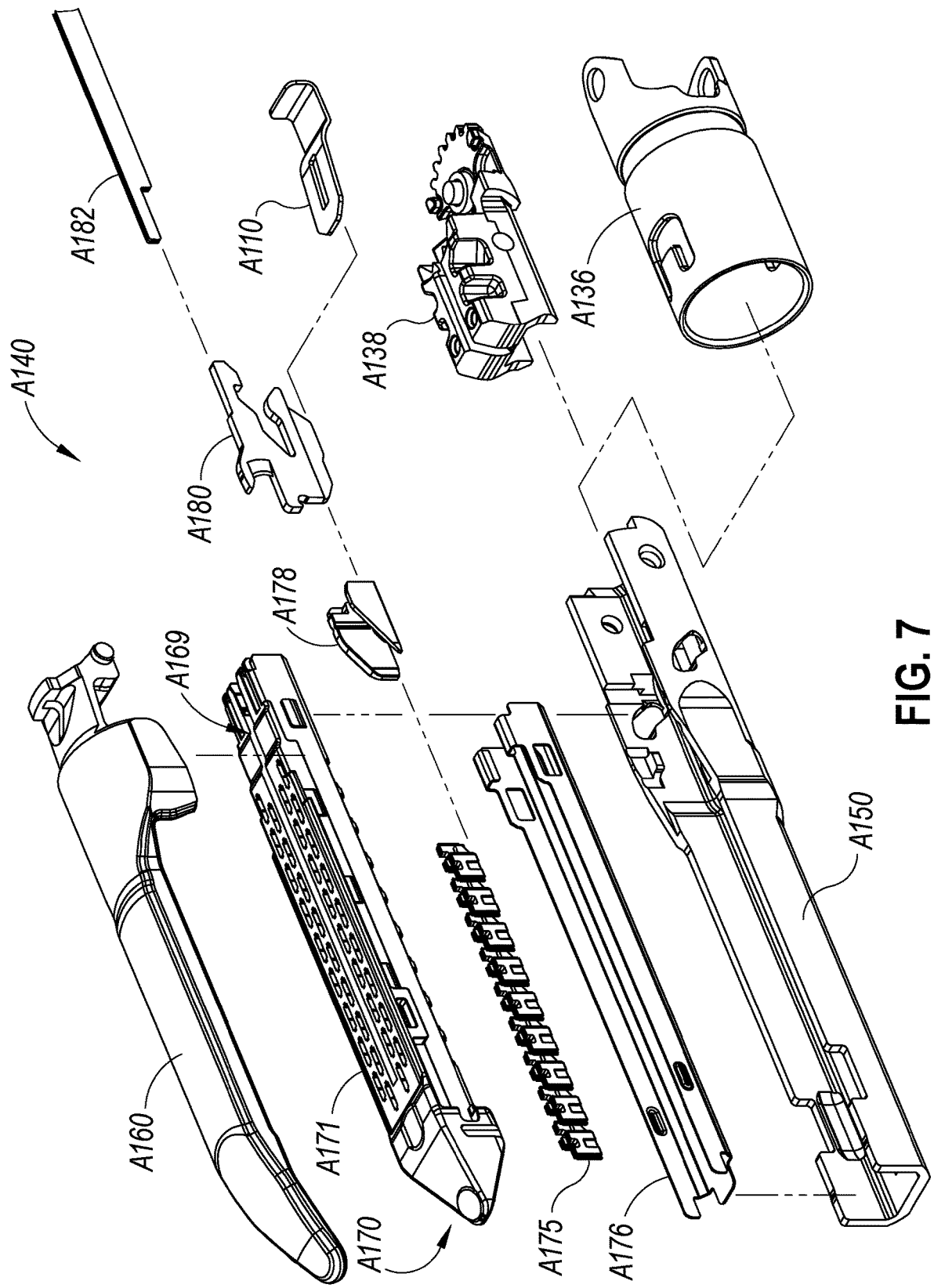
FIG. 7 depicts an exploded perspective view of another example of an end effector with a staple cartridge configured for use with the surgical stapler of FIG. 1.

FIG. 7 shows another illustrative end effector (140) that may be readily incorporated into surgical stapler (10) in place of end effector (40). End effector (140) includes a lower cartridge jaw (150), a pivotable anvil jaw (160), and a closure ring (A236), which are similar to cartridge jaw (42), anvil jaw (44), and closure ring (36) of end effector (40). A staple cartridge (170) similar to staple cartridge (70) may be removably installed into cartridge jaw (150) and includes a cartridge body (171), a lower cartridge pan (176), a sled (178), a plurality of staple drivers (175), and a plurality of staples (not shown) similar to staples (86). A firing beam (182) is coupled to a proximal end of knife (180) and is configured to drive knife (180) distally and/or proximally. A resilient member exemplified as a leaf spring (110) is positioned proximal to knife (180) and is configured to releasably engage and resiliently bias knife (180) downwardly. A frame member (138) supports leaf spring (110) and is positioned within closure ring (136) and is coupled to a proximal end of cartridge jaw (150) such that frame member (138) couples with an articulation joint similar to articulation joint (32).

Knife (180) includes a cutting edge (184), an upper extension (190), and a lower extension (186). Upper extension (190) extends proximally from cutting edge (184) and includes a downwardly extending tab (198) configured to lockingly engage frame member (138) such that frame member (138) may prevent tab (198) and knife (180) from advancing distally in the absence of an unspent staple cartridge (170), as will be described in greater detail below. Lower extension (186) extends proximally underneath cutting edge (184) and includes a distal end projection (197) and a distal wall (181). Distal end projection (197) extends distally and downwardly from lower extension (186) such that and underside of distal end projection (197) is configured to vertically engage an upwardly facing knife engagement surface at the proximal end of sled (178). Distal end projection (197) and distal wall (181) are configured to engage sled (178) when knife (180) is translated distally within cartridge jaw (150) to thereby drive sled (178) distally within cartridge jaw (150) to fire staple cartridge (170). A proximal portion of lower extension (186) includes a rounded tab that extends upwardly and is configured to engage leaf spring (110) such that leaf spring (110) may bias lower extension (186) and knife (180) downwardly so that tab (198) of upper extension (190) engages frame member (138) to prevent knife (180) from advancing distally in the absence of an unloaded staple cartridge (170).

Figure 8A:
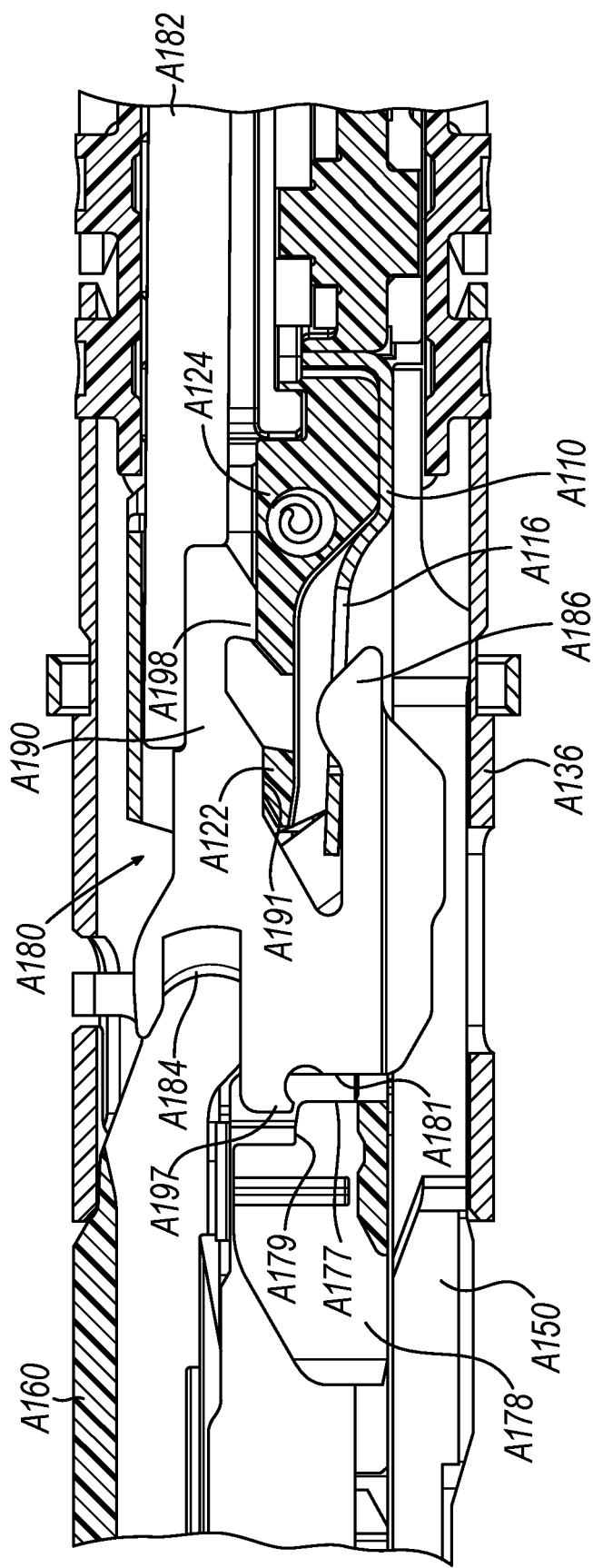
FIG. 8A depicts a side cross-sectional view of the end effector of FIG. 7, showing the compatible staple cartridge in an unspent state seated in a cartridge jaw, and showing a knife and a sled in unactuated proximal positions before firing of the unspent staple cartridge.
Figure 8B:
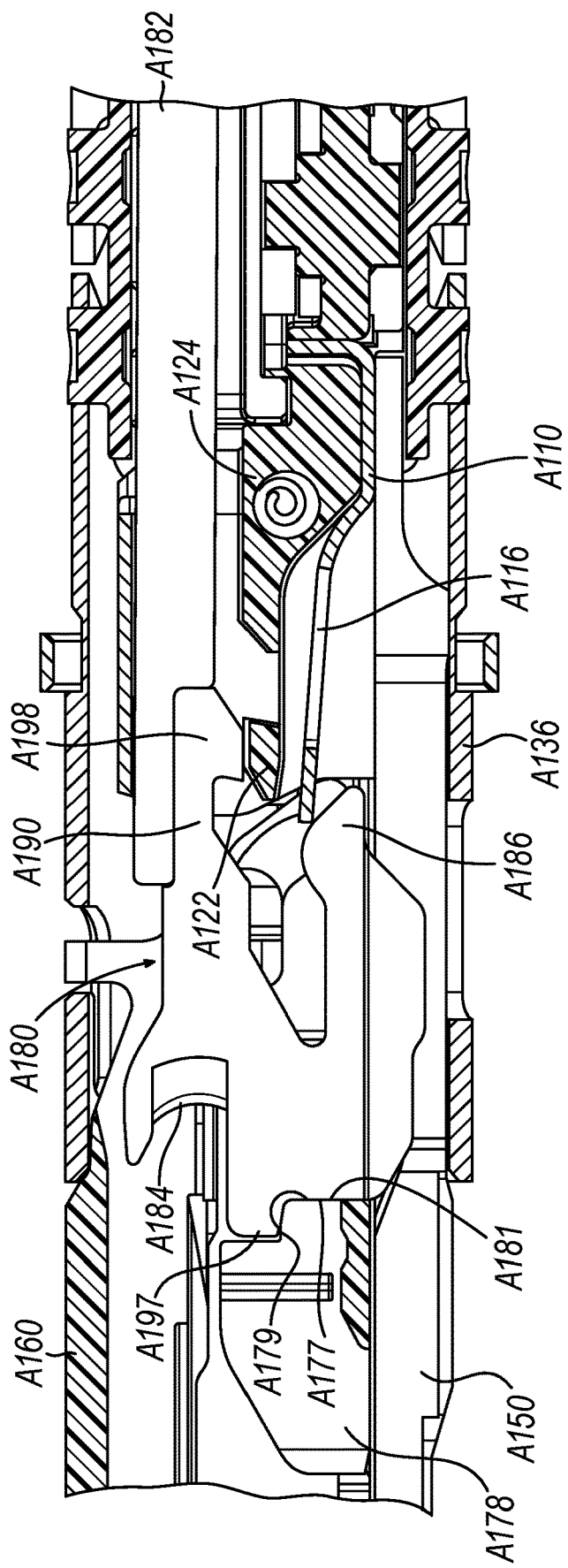
FIG. 8B depicts another side cross-sectional view of the end effector and unspent staple cartridge of FIG. 8A, showing distal actuation of the knife and sled to initiate firing of the unspent staple cartridge.

FIGS. 8A-8B show knife (180) being fired with an unspent staple cartridge (170) loaded in cartridge jaw (150) of end effector (140). FIG. 8A shows knife (180) in a proximal position in which upper extension (190) of knife (180) is positioned above engagement features (122, 124) of frame member (138). Wall (191) of upper extension (190) is resting on a top surface of first engagement feature (122), while tab (198) of upper extension (190) is resting on a top surface of second engagement feature (124). Leaf spring (110) is positioned between lower jaw (150) and frame member (138). An opening (116) of leaf spring (110) is positioned above lower extension (186) of knife (180) such that the tab of lower extension (186) tab is positioned within opening (116) of leaf spring (110).

As shown in FIG. 8B, in response to actuation of firing trigger (28), firing beam (182) drives knife (180) distally through staple cartridge (170), which in turn drives sled (178) distally through staple cartridge (170). As knife (180) is driven distally, a lower surface of distal end projection (197) of knife (180) engages an upwardly facing knife engagement surface (179) at the proximal end of sled (178), such that sled (178) vertically supports knife (180). Simultaneously, distal wall (181) of knife (180) engages a proximal end (177) of sled (178). Because sled (178) maintains the vertical position of knife (180) against the downward resilient bias of leaf spring (110), tab (198) of knife (180) translates distally above engagement features (122, 124) of frame member (138) and avoids falling into a lockout position between engagement features (122, 124), thus permitting end effector (140) to be fired.

Figure 9A:
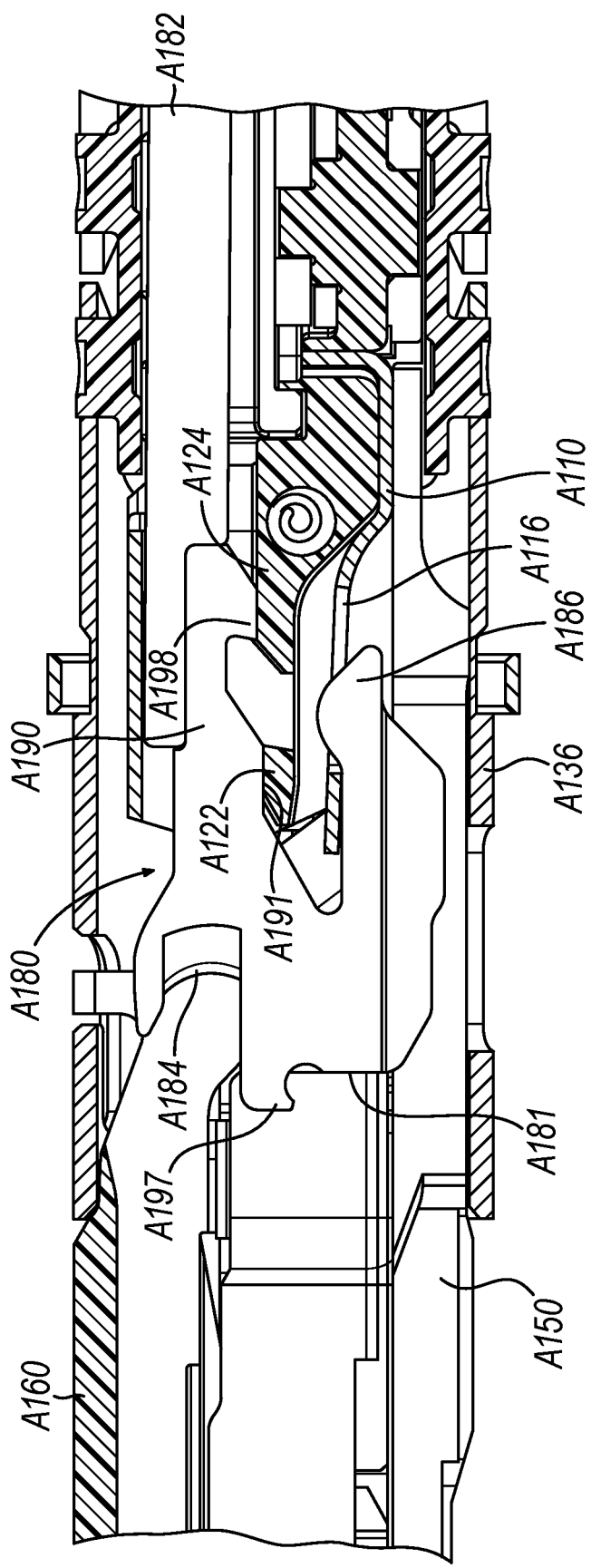
FIG. 9A depicts a side cross-sectional view of the end effector of FIG. 7, showing the staple cartridge in a spent state and the knife in an unactuated proximal position before attempted firing of the spent staple cartridge.
Figure 9B:
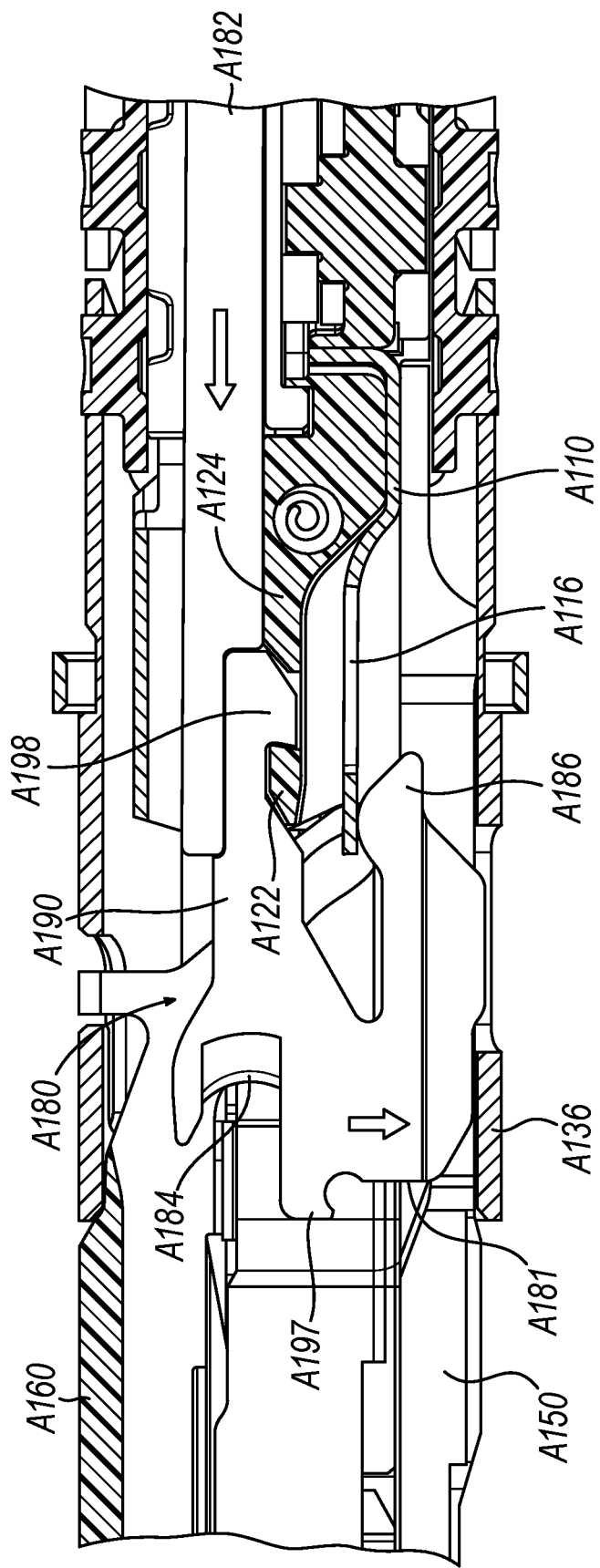
FIG. 9B depicts another side cross-sectional view of the end effector and spent staple cartridge of FIG. 9A, showing the knife assuming a lockout position in response to distal actuation of the knife by a firing beam.

After end effector (140) is fired, knife (180) is retracted to its proximal position and the spent staple cartridge (170) may be replaced with a fresh (aka unspent) staple cartridge (170). However, in some instances the user may forget to install an unspent staple cartridge (170). FIG. 9A shows an example of such a scenario in which knife (180) is positioned proximally, but a cartridge sled (178) is not, due to either a spent staple cartridge (170) being loaded in cartridge jaw (150) or a staple cartridge (170) being entirely absent from cartridge jaw (150). Accordingly, sled (178) is not vertically supported against the resilient bias of leaf spring (110). As a result, when knife (180) is actuated distally for an attempted firing stroke, tab (198) falls between engagement features (122, 124) of frame member (138), thus constraining tab (198) longitudinally in a lockout position such that knife (180) is inhibited from advancing sled (178) distally to fire staple cartridge (170). Accordingly, knife (180) is inhibited from severing the clamped tissue.

End effector (140) may be further configured and operable in accordance with the teachings of U.S. Pat. No. 10,335,147, entitled "Method of Using Lockout Features for Surgical Stapler Cartridge," issued Jul. 2, 2019, the disclosure of which is incorporated by reference herein in its entirety.

II. Illustrative Features for Inhibiting Use of an Incompatible Staple Cartridge with Surgical Stapler As discussed above in connection with FIGS. 7-9B, it may be desirable to inhibit actuation of the firing assembly of a surgical stapler if the end effector is loaded with spent staple cartridge, and also if a staple cartridge is entirely absent from the end effector. Additionally, it may also be desirable to inhibit use of an incompatible staple cartridge with a surgical stapler, including where the incompatible staple cartridge is in an unspent state and is capable of being at least partially seated within the cartridge jaw of the surgical stapler end effector.

The illustrative safety features shown and described below in connection with FIGS. 10-21 provide at least two barriers to such misuse by a clinician. As described in greater detail below, the first safety feature inhibits a distal end portion of an incompatible staple cartridge from being substantially seated within the cartridge jaw. The second safety feature serves as a fallback to the first safety feature and inhibits a firing driver of the surgical stapler from driving a sled of the incompatible staple cartridge to deploy staples, even when the incompatible staple cartridge is unspent and its sled is in a proximal undisplaced position.

A. Staple Cartridge Lugs That Inhibit Full Seating of Staple Cartridge

Figure 10:
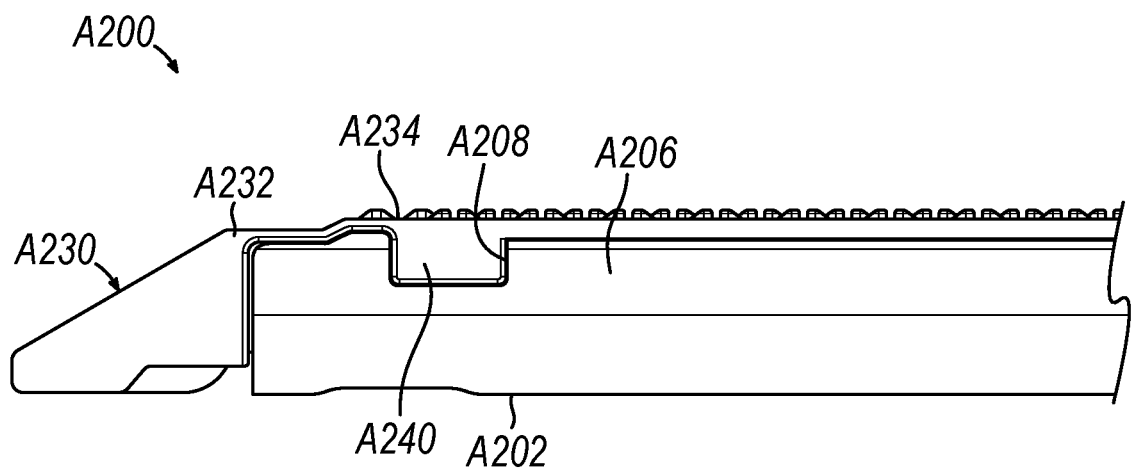
FIG. 10 depicts a side elevational view of a first cartridge jaw of an alternative first surgical stapler properly loaded with a first staple cartridge configured for use with the first surgical stapler.

FIG. 10 shows a first cartridge jaw (A202) of a first end effector (A200) (see FIG. 15), and a corresponding first staple cartridge (A230) intended for use with first end effector (A200) such that first end effector (A200) and first staple cartridge (A230) are compatible. First staple cartridge (A230) includes a first cartridge body (A232) that defines a first deck (A234) and includes a plurality of cartridge pockets (not shown) that house a corresponding plurality of staples (not shown) and a corresponding plurality of staple drivers (not shown). First staple cartridge (A230) further includes a first pan (A236) and a first sled (A238) slidably coupled with first cartridge body (A232) and constrained vertically by first pan (A236).

Figure 11:
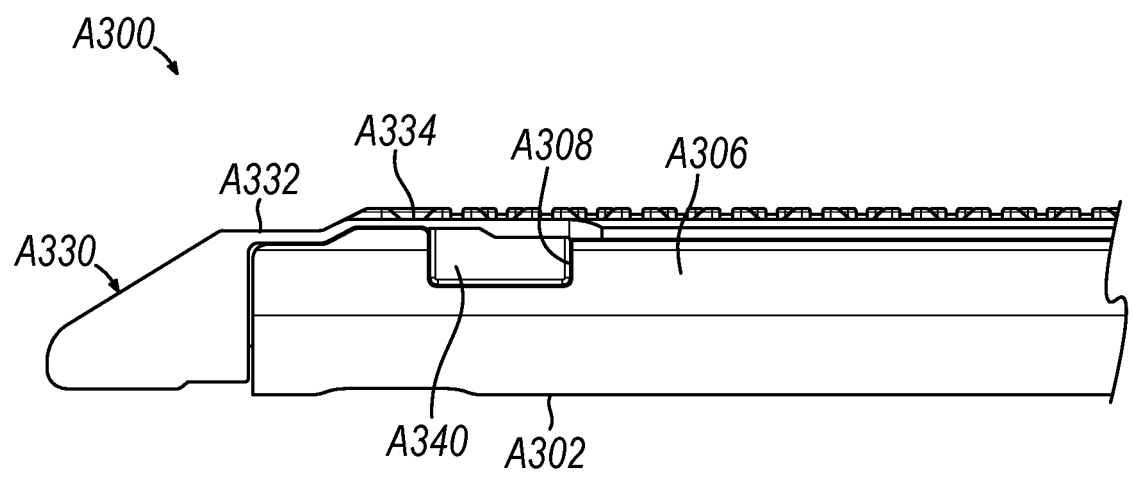
FIG. 11 depicts a side elevational view of a second cartridge jaw of an alternative second surgical stapler properly loaded with a second staple cartridge configured for use with the second surgical stapler.

Similarly, FIG. 11 shows a second cartridge jaw (A302) of a second end effector (A300) (see FIG. 16), and a corresponding second staple cartridge (A330) configured for use with second end effector (A300). Second staple cartridge (A330) includes a second cartridge body (A332) that defines a second deck (A334) and includes a plurality of cartridge pockets (not shown) that house a corresponding plurality of staples (not shown) and a corresponding plurality of staple drivers (not shown). Second staple cartridge (A330) further includes a second pan (A336) and a second sled (A338) slidably coupled with second cartridge body (A332) and constrained vertically by second pan (A336).

In the present example, first staple cartridge (A230) has exterior dimensions that are substantially equal to those of second staple cartridge (A330). For instance, first staple cartridge (A230) has a first maximum width and second staple cartridge (A330) has a second maximum width that is substantially equal to the first maximum width. However, first staple cartridge (A230) is specifically configured to cooperate with a first anvil jaw (A204) (see FIG. 15) of first end effector (A200) to form staples with a two-dimensional shape. In contrast, second staple cartridge (A330) is specifically configured to cooperate with a second anvil jaw (A304) (see FIG. 16) of second end effector (A300) to form staples with a three-dimensional shape. Examples of such a three-dimensional formed staple shape and corresponding staple forming features are disclosed in U.S. Pat. No. 11,406,379, entitled "Surgical End Effectors with Staple Cartridges," issued Aug. 9, A2022, the disclosure of which is incorporated by reference herein in its entirety. Due to structural differences in the two-dimensional staple forming features of first anvil jaw (A204) and first staple cartridge (A230) and relative to the three-dimensional staple forming features of second anvil jaw (A304) and second staple cartridge (A330), attempted use of first staple cartridge (A230) in second end effector (A300) or second staple cartridge (A330) in first end effector (A200) would yield malformed staples that are ineffective to seal patient tissue being fired upon.

First cartridge jaw (A202) includes a pair of first sidewalls (A206) each having a first compatibility recess (A208) that opens to an upper edge of the first sidewall (A206). Each first compatibility recess (A208) is suitably sized, shaped, and located to receive a respective first compatibility lug (A240) that protrudes laterally from a corresponding side of first cartridge body (A232), thereby permitting a distal end portion of first staple cartridge (A230) to be substantially seated within first cartridge jaw (A202). Similarly, second cartridge jaw (A302) includes a pair of second sidewalls (A306) each having a second compatibility recess (A308) that opens to an upper edge of the second sidewall (A306). Each second compatibility recess (A308) is suitably sized, shaped, and located to receive a respective second compatibility lug (A340) that protrudes laterally from a corresponding side of a second cartridge body (A332), thereby permitting a distal end portion of second staple cartridge (A330) to be substantially seated within second cartridge jaw (A302). While first and second compatibility lugs (A240, A340) are shown as generally rectangular in the present example, they may be formed with various other shapes in other examples.

Figure 12:
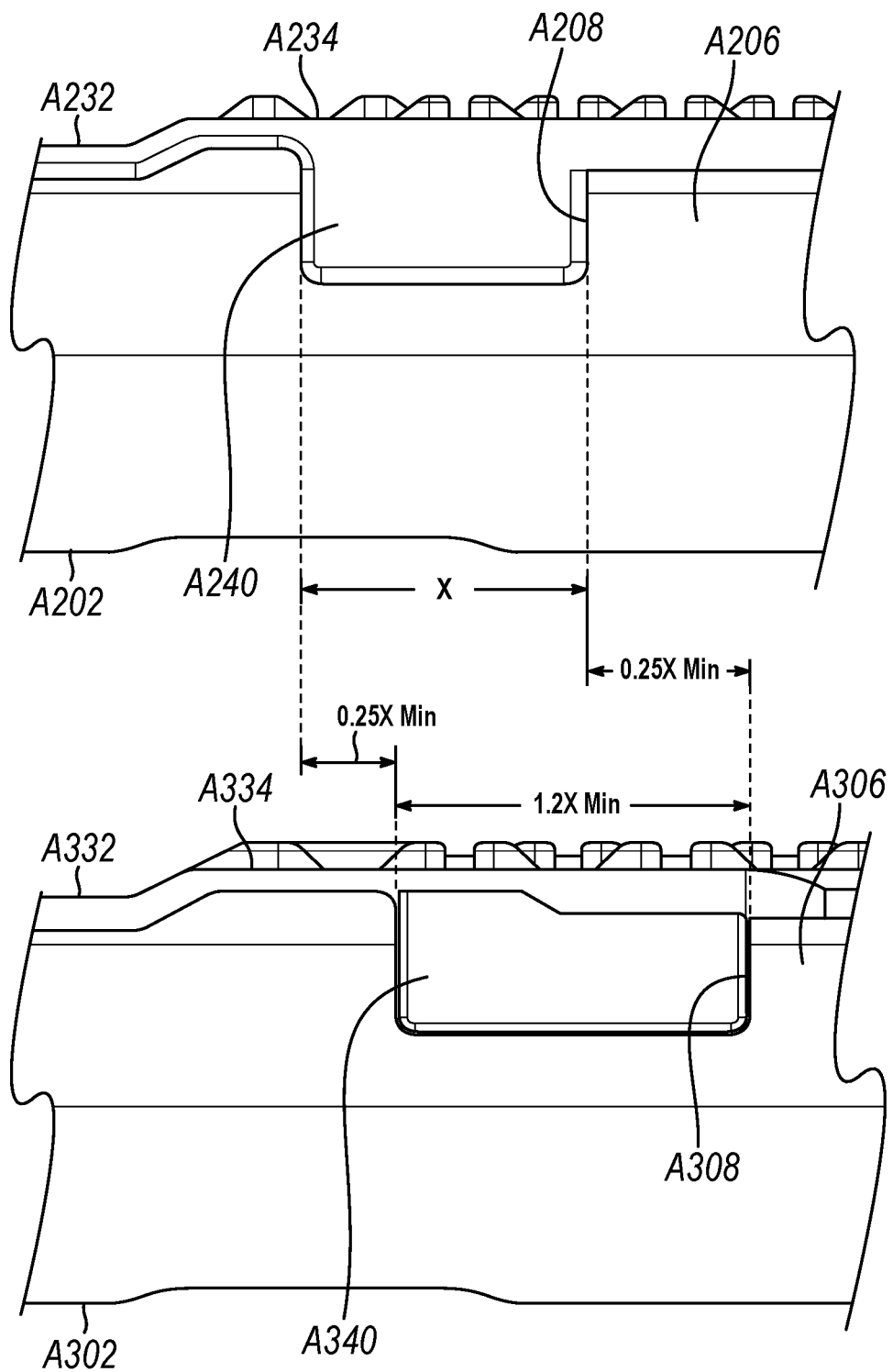
FIG. 12 depicts an enlarged side elevational view of the first cartridge jaw and first staple cartridge of FIG. 10 positioned alongside the second cartridge jaw and second staple cartridge of FIG. 11, showing a dimensional comparison of corresponding lugs of the cartridges and recesses of the cartridge jaws.

Each first compatibility lug (A240) of first staple cartridge (A230) and its respective first compatibility recess (A208) of first cartridge jaw (A202) differ from the corresponding second compatibility lug (A340) of second staple cartridge (A330) and its respective second compatibility recess (A308) of second cartridge jaw (A302) in at least one of size, shape, or longitudinal location. More specifically, as shown in FIG. 12, each first compatibility lug (A240) differs from the corresponding second compatibility lug (A340) in length and longitudinal location. In particular, second compatibility lug (A340) is approximately 20% longer than first compatibility lug (A240) and is proximally displaced relative to second compatibility lug (A340) such that a distal end of second compatibility lug (A340) is displaced proximal to a distal end of first compatibility lug (A240) by a longitudinal distance equal to at least approximately 25% of the length of first compatibility lug (A240). Similarly, a proximal end of second compatibility lug (A340) is displaced proximal to a proximal end of first compatibility lug (A240) by a longitudinal distance equal to at least approximately 25% of the length of first compatibility lug (A240).

Figure 13:
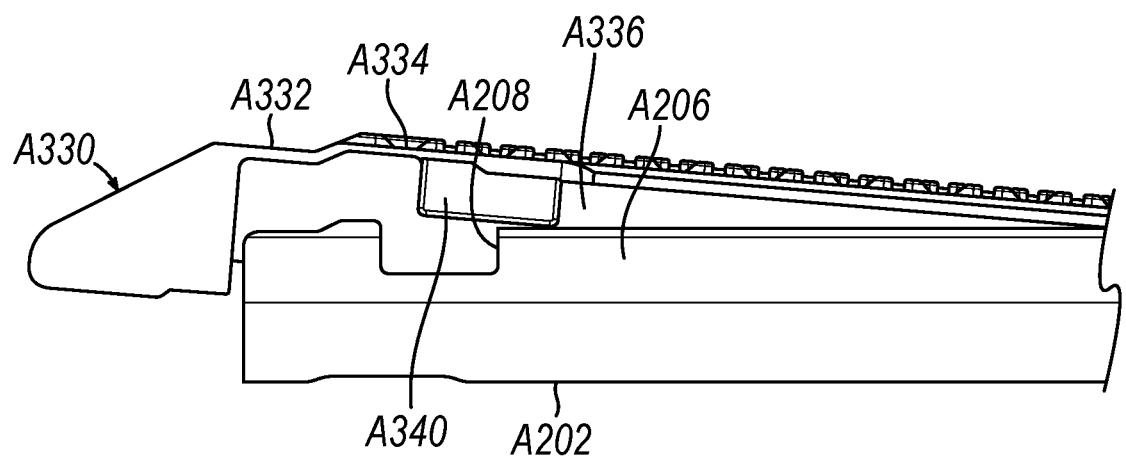
FIG. 13 depicts a side elevational view of the second staple cartridge partially seated within the first cartridge jaw as a result of user error, where the lug of the second staple cartridge is non-receivable by the recess of the first cartridge jaw such that only a proximal end portion of the second staple cartridge is substantially seated within the first cartridge jaw.
Figure 14:
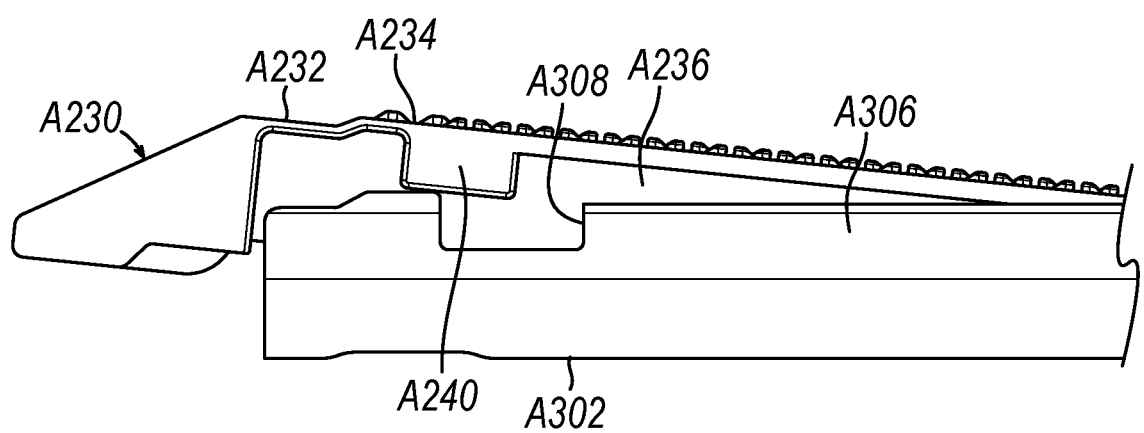
FIG. 14 depicts a side elevational view of the first staple cartridge partially seated within the second cartridge jaw as a result of user error, where the lug of the first staple cartridge is non-receivable by the recess of the second cartridge jaw such that only a proximal end portion of the first staple cartridge is substantially seated within the second cartridge jaw.

As shown in FIGS. 13-14, the structural differences between first compatibility lugs (A240) of first staple cartridge (A230) and second compatibility lugs (A340) of second staple cartridge (A330) described above render first compatibility recesses (A208) of first cartridge jaw (A202) incapable of receiving second compatibility lugs (A340), and render second compatibility recesses (A308) of second staple cartridge (A330) incapable of receiving first compatibility lugs (A240). Accordingly, the distal end portion of second staple cartridge (A330) is incapable of being substantially seated within first cartridge jaw (A202), as depicted in FIG. 13 where an underside of second compatibility lug (A340) is shown abutting an upper edge of first sidewall (A206) proximal to first compatibility recess (A208). Similarly, the distal end portion of first staple cartridge (A230) is incapable of being substantially seated within second cartridge jaw (A302), as depicted in FIG. 14 where an underside of first compatibility lug (A240) is shown abutting an upper edge of second sidewall (A306) distal to second compatibility recess (A308). Advantageously, this provides a clear visual indication to the clinician that first staple cartridge (A230) is incompatible with second end effector (A300) and that second staple cartridge (A330) is incompatible with first end effector (A200) such that the clinician should not proceed with conducting a surgical procedure with such a mis-matched cartridge-stapler configuration.

B. Staple Cartridge Sled Features that Promote Firing Lockout when Loaded in Incompatible Stapler While first and second cartridge jaw recesses (A208, A308) and first and second staple cartridge lugs (A240, A240) described above are specifically designed to provide a clear visual indication to a clinician of cartridge incompatibility when a staple cartridge (A230, A330) is loaded into an incompatible end effector (A300, A200), a clinician may nonetheless attempt to fire on patient tissue with the incompatible cartridge-stapler combination. The illustrative features described below in connection with FIGS. 15-21 provide a firing lockout condition to inhibit firing in such a scenario of clinician misuse.

Figure 15:
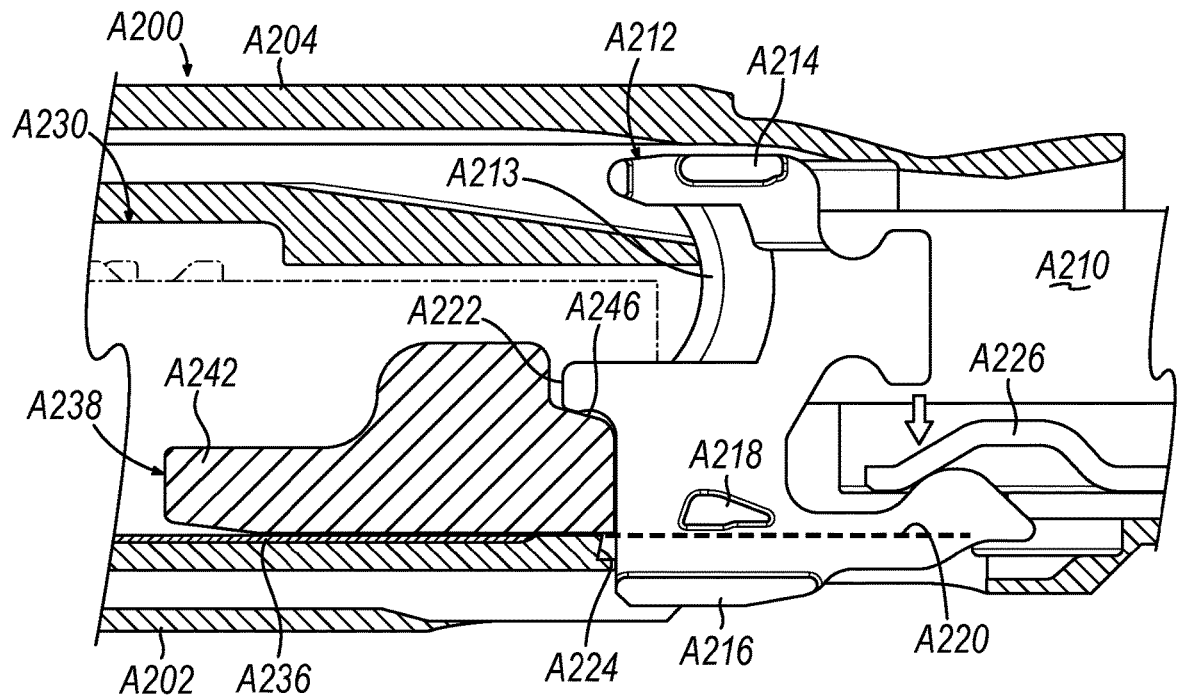
FIG. 15 depicts a partial side cross-sectional view of the end effector of the first surgical stapler properly loaded with the first staple cartridge of FIG. 10 in an unspent state, showing a sled of the first staple cartridge vertically supporting a distal end projection of the knife of the first surgical stapler to bypass a knife lockout position and permit firing.

FIG. 15 shows first staple cartridge (A230) in an unspent and undisturbed state such that first sled (A238) is positioned in a proximal undisplaced position, where first staple cartridge (A230) has been substantially seated within first cartridge jaw (A202) of first end effector (A200) such that first anvil jaw (A204) has been permitted to fully close onto tissue (not shown) positioned between first anvil jaw (A204) and first staple cartridge (A230). As shown in FIG. 15, first end effector (A200) includes a first firing beam (A210) and a first knife (A212) secured to a distal end of first firing beam (A210). First knife (A212) includes a cutting edge (A213), a transversely oriented upper protrusion (A214) slidable within a longitudinal slot of first anvil jaw (A204), a transversely oriented lower protrusion (A216) slidable within a longitudinal slot of first cartridge jaw (A202), and a transversely oriented middle protrusion (A218) slidable along a floor (A220) of first cartridge jaw (A202). First knife (A212) further includes a first distal end projection (A222) configured to be vertically supported by a first knife engagement surface (A246) of first sled (A238), as described in greater detail below. First end effector (A200) further includes a first lockout recess (A224) formed in first cartridge jaw floor (A220) at its proximal end, and a first lockout spring (A226) positioned proximal to first lockout recess (A224) and configured to bias first knife (A212) downwardly toward first cartridge jaw floor (A220) such that middle protrusion (A218) of first knife (A212) is biased downwardly toward first lockout recess (A224).

Figure 20:
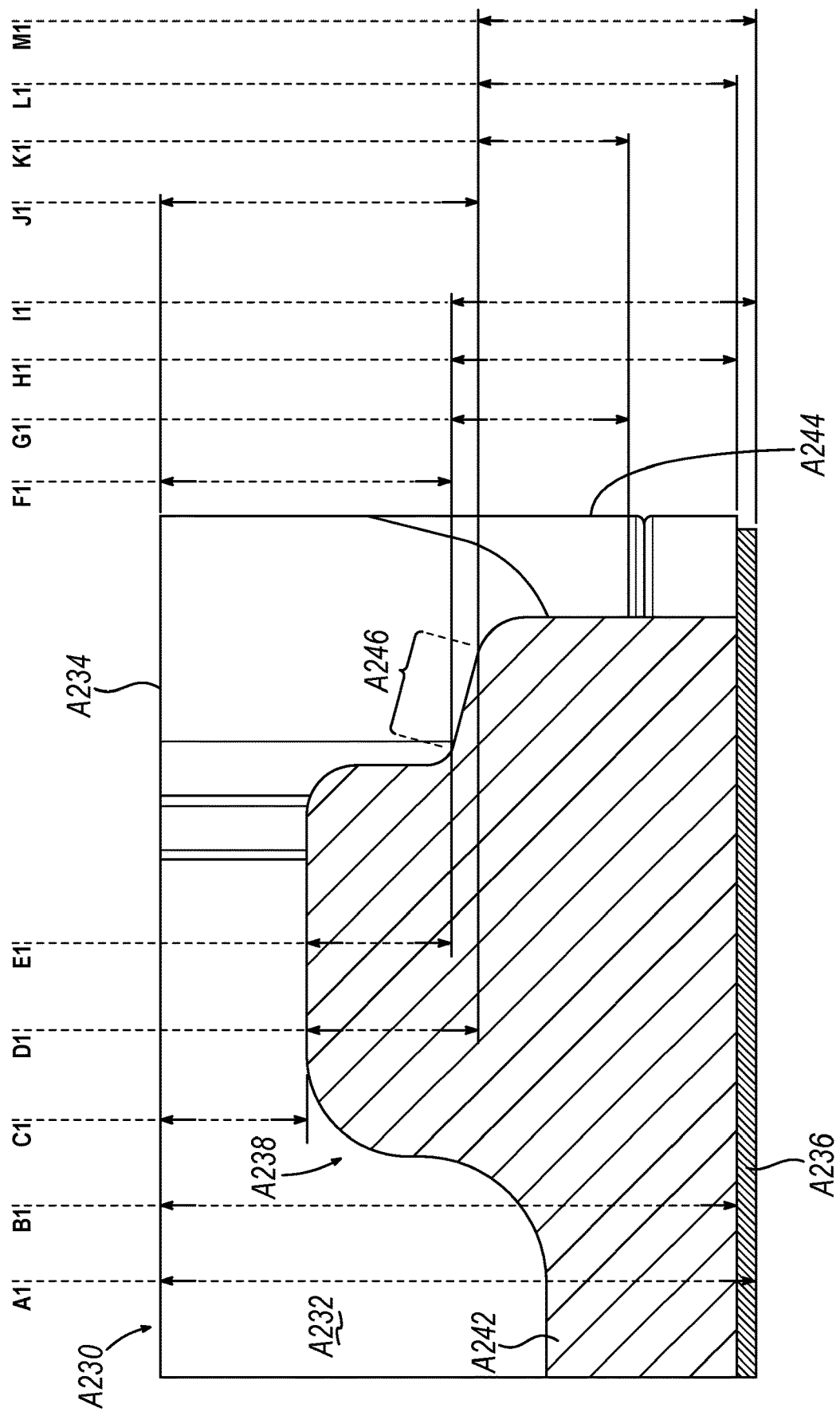
FIG. 20 depicts a partial side cross-sectional view of a proximal portion of the first staple cartridge of FIG. 10, showing select dimensions.

As shown in FIGS. 15 and 20, first sled (A238) of first staple cartridge (A230) includes a first central body portion (A242) and a pair of first fins (A244) (see FIG. 20) disposed on each lateral side of first central body portion (A242). Though not shown, each first fin (A244) includes an angled distal surface configured to cammingly engage a respective row of staple drivers of first staple cartridge (A230) and actuate the staple drivers upwardly to thereby deploy staples from the cartridge pockets as first sled (A238) is driven distally within first staple cartridge (A230) during a firing stoke. A proximal end of first central body portion (A242) is recessed distally relative to first fins (A244) and defines a first knife engagement surface (A246) that is substantially planar and angled downwardly in a proximal direction.

As shown in FIG. 15, first sled (A238) is in its proximal undisplaced position such that first knife engagement surface (A246) directly contacts an underside of first distal end projection (A222) to vertically support first knife (A212) in an upward direction and thereby overcome the downward bias imposed by first lockout spring (A226). As a result, in response to a clinician's firing input, first firing beam (A210) may then actuate first knife (A212) distally within first end effector (A200), which in turn drives first sled (A238) distally within first staple cartridge (A230) to deploy staples into the clamped tissue. If first sled (A238) were positioned distal to its proximal undisplaced position, for example as a result of first staple cartridge (A230) having been previously fired or first sled (A238) having been bumped distally during handling or transport, then first knife (A212) would assume a lockout position in response to attempted firing of first end effector (A200). Specifically, first sled (A238) would not be appropriately positioned to vertically support first knife (A212), which would in turn drop downwardly under the bias of first lockout spring (A226) such that middle protrusion (A218) of first knife (A212) would advance downwardly and distally into first lockout recess (A224), which would inhibit further distal advancement of first knife (A212).

Figure 16:
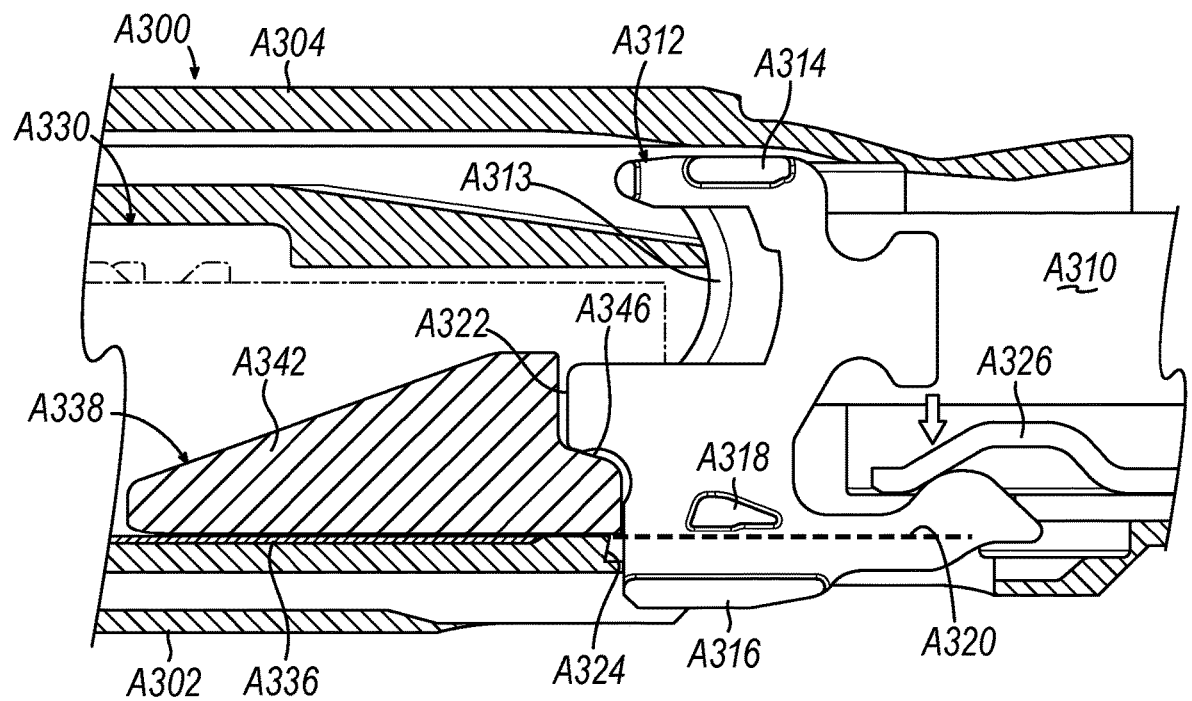
FIG. 16 depicts a partial side cross-sectional view of the end effector of the second surgical stapler properly loaded with the second staple cartridge of FIG. 11 in an unspent state, showing a sled of the second staple cartridge vertically supporting a distal end projection of the knife of the second surgical stapler to bypass a knife lockout position and permit firing.

FIG. 16 shows second staple cartridge (A330) in an unspent and undisturbed state such that second sled (A338) is positioned in a proximal undisplaced position, where second staple cartridge (A330) has been substantially seated within second cartridge jaw (A302) of second end effector (A300) such that second anvil jaw (A304) has been permitted to fully close onto tissue (not shown) positioned between second anvil jaw (A304) and second staple cartridge (A330). Similar to first end effector (A200), second end effector (A300) includes a second firing beam (A310) and a second knife (A312) secured to a distal end of second firing beam (A310). Second knife (A312) includes a cutting edge (A313), a transversely oriented upper protrusion (A314) slidable within a longitudinal slot of second anvil jaw (A304), a transversely oriented lower protrusion (A316) slidable within a longitudinal slot of second cartridge jaw (A302), and a transversely oriented middle protrusion (A318) slidable along a floor (A320) of second cartridge jaw (A302). Second knife (A312) further includes a second distal end projection (A322) configured to be vertically supported by a second knife engagement surface (A346) of second sled (A338), as described in greater detail below. Second end effector (A300) further includes a second lockout recess (A324) formed in second cartridge jaw floor (A320) at its proximal end, and a second lockout spring (A326) positioned proximal to second lockout recess (A324) and configured to bias second knife (A312) downwardly toward second cartridge jaw floor (A320) such that middle protrusion (A318) of second knife (A312) is biased downwardly toward second lockout recess (A324).

Figure 21:
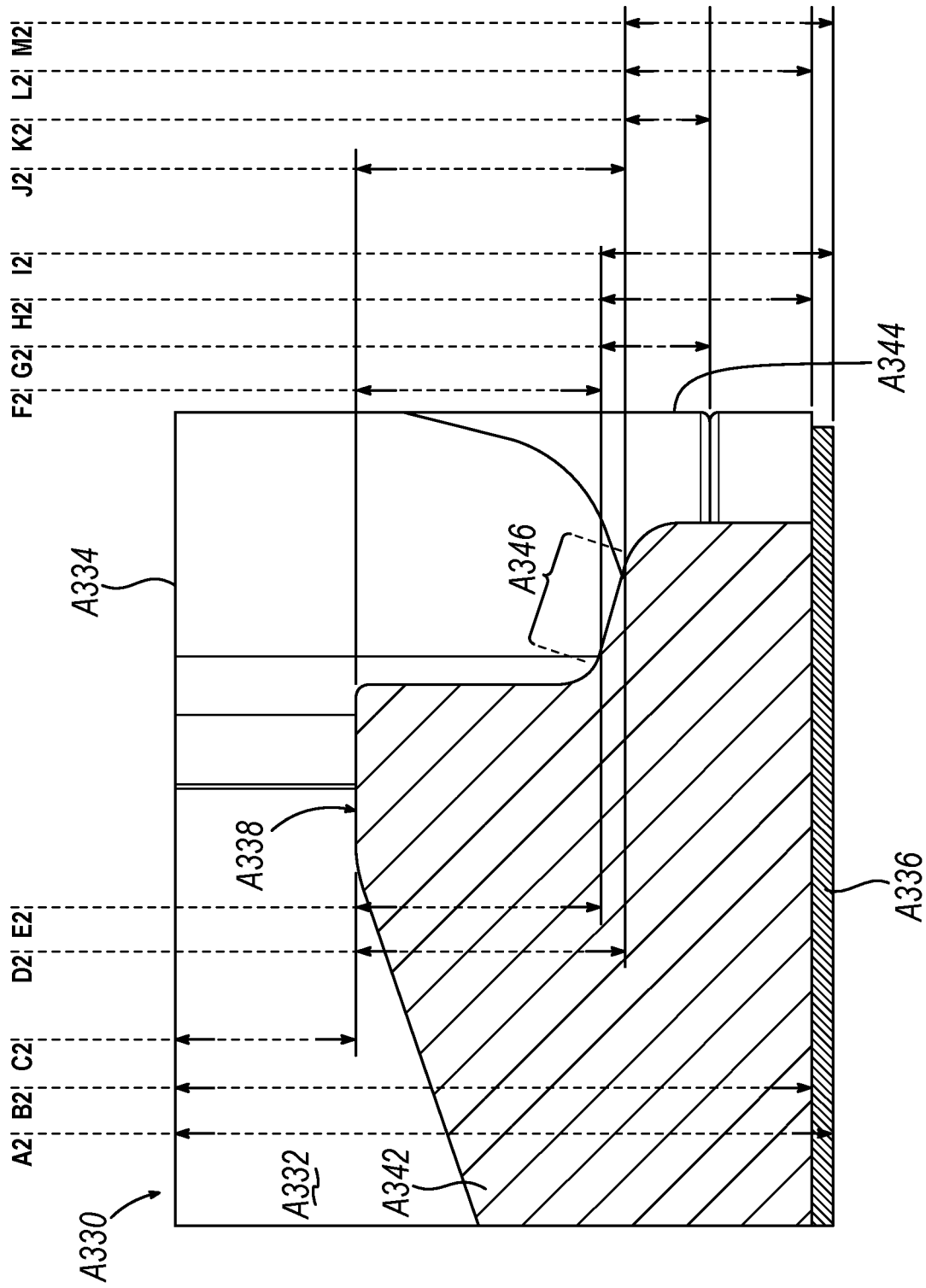
FIG. 21 depicts a partial side cross-sectional view of a proximal portion of the second staple cartridge of FIG. 11, showing select dimensions.

As shown in FIGS. 16 and 21, second sled (A338) of second staple cartridge (A330) includes a second central body portion (A342) and a pair of second fins (A344) (see FIG. 20) disposed on each lateral side of second central body portion (A342). Similar to first fins (A244), each second fin (A344) includes an angled distal surface configured to cammingly engage a respective row of staple drivers of second staple cartridge (A330) and actuate the staple drivers upwardly to thereby deploy staples from the cartridge pockets as second sled (A338) is driven distally within second staple cartridge (A330) during a firing stoke. A proximal end of second central body portion (A342) is recessed distally relative to second fins (A344) and defines a second knife engagement surface (A346) that is substantially planar and angled downwardly in a proximal direction. Second sled (A338) may be further configured in accordance with one or more teachings of U.S. Pat. No. 11,540,826, entitled "Surgical Stapler End Effector Sled Having Cartridge Wall Support Feature," issued Jan. 3, A2023, the disclosure of which is incorporated by reference herein in its entirety.

As shown in FIG. 16, second sled (A338) is in its proximal undisplaced position such that second knife engagement surface (A346) directly contacts an underside of second distal end projection (A322) to vertically support second knife (A312) in an upward direction and thereby overcome the downward bias imposed by second lockout spring (A326). As a result, in response to a clinician's firing input, second firing beam (A310) may then actuate second knife (A312) distally within second end effector (A300), which in turn drives second sled (A338) distally within second staple cartridge (A330) to deploy staples into the clamped tissue. If second sled (A338) were positioned distal to its proximal undisplaced position, for example as a result of second staple cartridge (A330) having been previously fired or second sled (A338) having been bumped distally during handling or transport, then second knife (A312) would assume a lockout position in response to attempted firing of second end effector (A300). Specifically, second sled (A338) would not be appropriately positioned to vertically support second knife (A312), which would in turn drop downwardly under the bias of second lockout spring (A326) such that middle protrusion (A318) of second knife (A312) would advance downwardly and distally into second lockout recess (A324), which would inhibit further distal advancement of second knife (A312).

As shown in FIGS. 17-21, first and second end effectors (A200, A300) and first and second staple cartridges (A230, A330) are configured such that first staple cartridge (A230) may be fired only by first end effector (A200) and second staple cartridge (A330) may be fired only by second end effector (A300). In other words, first end effector (A200) is incapable of firing second staple cartridge (A330) and second end effector (A300) is incapable of firing first staple cartridge (A230), even when first and second sleds (A238, A338) are located in their proximal undisplaced positions. This functionality is provided by strategically designed structural differences between first and second knives (A212, A312) and first and second sleds (A238, A338), as described below.

Figure 17:
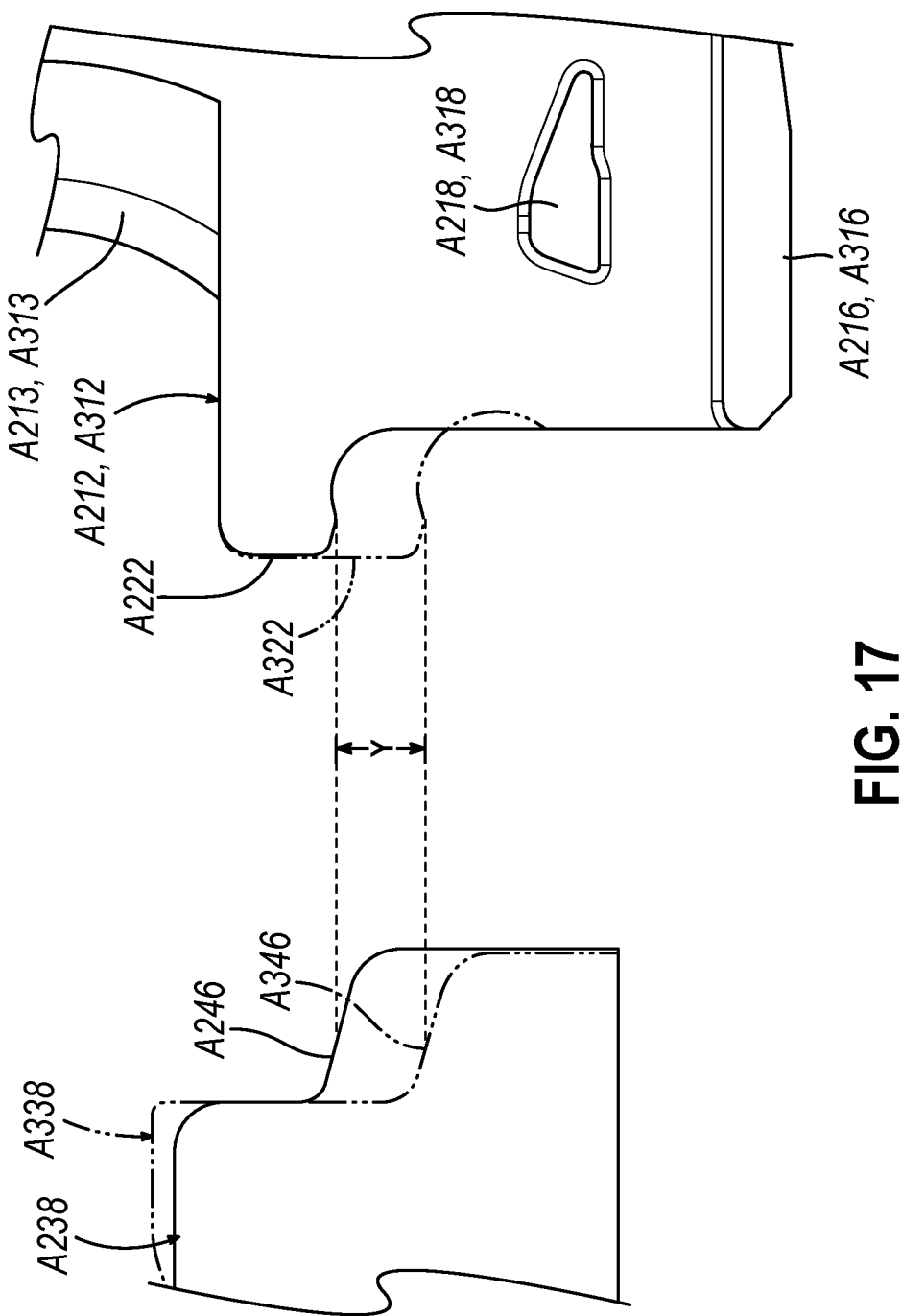
FIG. 17 depicts a partial side elevational view of the sleds of the first and second cartridges and the knives of the first and second surgical staplers of FIGS. 15 and 16, showing differing features of the second sled and the second knife in phantom relative to the corresponding features of the first sled and the first knife, where such differences inhibit firing of the first staple cartridge by the second surgical stapler and firing of the second staple cartridge by the first surgical stapler.

As shown in FIG. 17, second knife engagement surface (A346) of second sled (A338) is positioned lower than first knife engagement surface (A246) of first sled (A238), relative to a bottom surface of each sled (A238, A338), by a vertical distance (Y). Additionally, second distal end projection (A322) of second knife (A312) is vertically thicker than second distal end projection (A322) of second knife (A312) such that the sled-contacting underside of second distal end projection (A322) is positioned lower than the sled-contacting underside of first distal end projection (A222) of first knife (A212), relative to a top surface of each distal end projection (A222, A322), by vertical distance (Y). First and second knife engagement surfaces (A246, A346) are substantially parallel to one another such that vertical distance (Y) may be evaluated at any longitudinal location along knife engagement surfaces (A246, A346). In the present example, vertical distance (Y) is approximately 0.030 in (0.76 mm) as calculated from the dimensions provided below in Table 1 in connection with FIGS. 20 and 21.

Accordingly, first sled (A238) is capable of vertically supporting only first distal end projection (A222) of first knife (A212), and not second distal end projection (A322) of second knife (A312), in a manner sufficient to bypass the lockout state of first knife (A212) during an attempted firing stroke on first staple cartridge (A230). Similarly, second sled (A338) is capable of vertically supporting only second distal end projection (A322) of second knife (A312), and not first distal end projection (A222) of first knife (A212), in a manner sufficient to bypass the lockout state of second knife (A312) during an attempted firing stroke on second staple cartridge (A330).

Figure 18A:
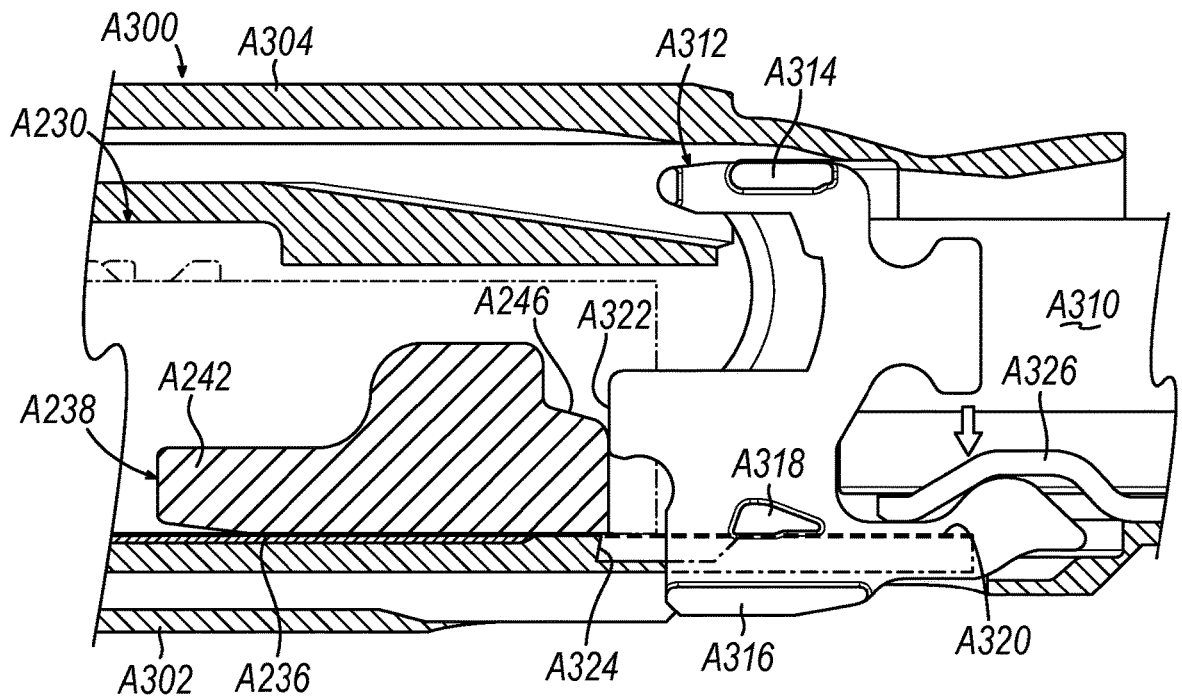
FIG. 18A depicts a partial side cross-sectional view of the second surgical stapler end effector of FIG. 16 improperly loaded with the first staple cartridge of FIG. 10 as a result of user error, showing the knife and sled in unactuated proximal positions before attempted firing.
Figure 18B:
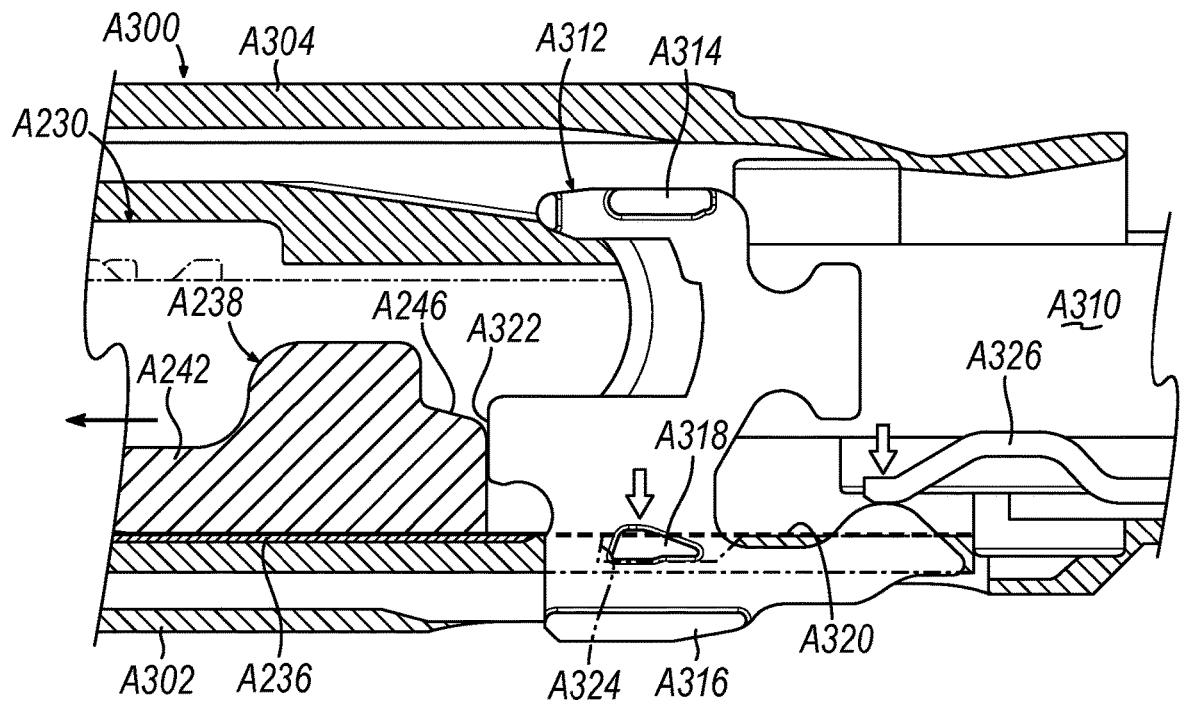
FIG. 18B depicts another partial side cross-sectional view of the second surgical stapler end effector and first staple cartridge of FIG. 18A, showing the knife advanced distally into a lockout position as a result of attempted firing.

FIGS. 18A-18B show an illustrative case of clinician misuse in which a clinician has installed first staple cartridge (A230) into second cartridge jaw (A302) of second end effector (A300). As shown and described above in connection with FIG. 14, only the proximal end portion of first staple cartridge (A230) is capable of being substantially seated in second cartridge jaw (A302), whereas its distal end portion is inhibited from being substantially seated due to the inability of second compatibility recesses (A308) of second cartridge jaw (A302) to receive first compatibility lugs (A240) of first staple cartridge (A230). Accordingly, first staple cartridge (A230) is capable of being only partially seated within second cartridge jaw (A302). Nevertheless, because the proximal end portion of first staple cartridge (A230) is substantially seated within second cartridge jaw (A302) and first sled (A238) is in its proximal undisplaced position, it is desirable to actively inhibit second knife (A312) from driving first sled (A238) distally enough to deploy staples from first staple cartridge (A230) and yield malformation of the deployed staples against second anvil jaw (A304). The structural uniqueness of first sled (A238) and first knife (A212) relative to second sled (A338) and second knife (A312) as discussed above provides such a safeguard.

As shown in FIGS. 17 and 18A, an entirety of first knife engagement surface (A246) of first sled (A238) is positioned higher than the sled-contacting underside of second distal end projection (A322) of second knife (A312) by vertical distance (Y), such that first knife engagement surface (A246) is incapable of vertically supporting second distal end projection (A322). Rather, a distal end surface of second distal end projection (A322) abuts a proximal end surface of first sled (A238). In response to an attempted firing stroke by the clinician, second knife (A312) advances distally and drives first sled (A238) distally a minute distance while second lockout spring (A326) biases second knife (A312) downwardly against second cartridge jaw floor (A320). As shown in FIG. 18B, before first sled (A238) engages any staple drivers to deploy staples from first staple cartridge (A230), middle protrusion (A318) of second knife (A312) advances downwardly into second lockout recess (A324), which inhibits further distal advancement of second knife (A312) and thus halts firing of the incompatible first staple cartridge (A230).

Figure 19:
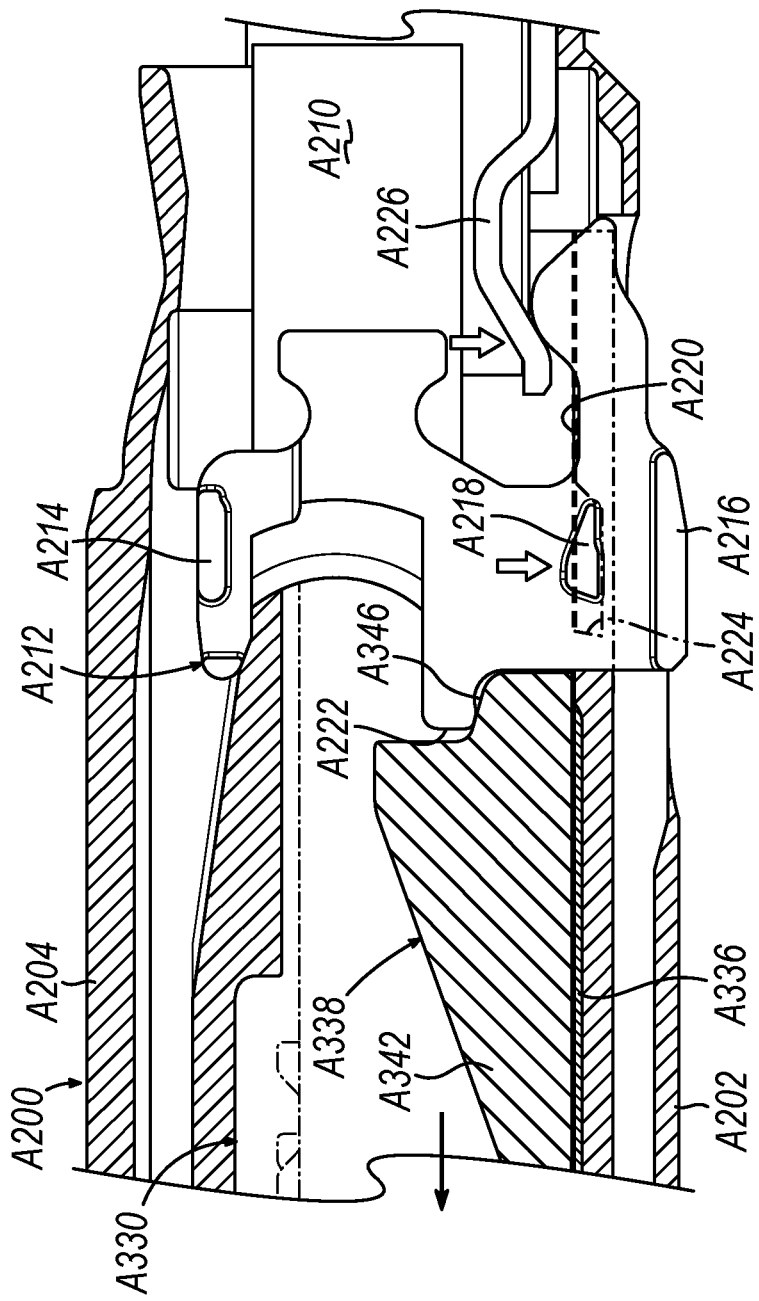
FIG. 19 depicts a partial side cross-sectional view of the first surgical stapler end effector of FIG. 15 improperly loaded with the second staple cartridge of FIG. 11 as a result of user error, showing the knife advanced distally into a lockout position as a result of attempted firing.

FIG. 19 shows another illustrative case of clinician misuse in which a clinician has installed second staple cartridge (A330) into first cartridge jaw (A202) of first end effector (A200). As shown and described above in connection with FIG. 13, only the proximal end portion of second staple cartridge (A330) is capable of being substantially seated in first cartridge jaw (A202), whereas its distal end portion is inhibited from being substantially seated due to the inability of first compatibility recesses (A208) of first cartridge jaw (A202) to receive second compatibility lugs (A340) of second staple cartridge (A330). Accordingly, second staple cartridge (A330) is capable of being only partially seated within first cartridge jaw (A202). Nevertheless, because the proximal end portion of second staple cartridge (A330) is substantially seated within first cartridge jaw (A202) and second sled (A338) is in its proximal undisplaced position, it is desirable to actively inhibit first knife (A212) from driving second sled (A338) distally enough to deploy staples from second staple cartridge (A330) and yield malformation of the deployed staples against first anvil jaw (A204). The structural uniqueness of first sled (A238) and first knife (A212) relative to second sled (A338) and second knife (A312) as discussed above provides such a safeguard.

As shown in FIG. 17, an entirety of second knife engagement surface (A346) of second sled (A338) is spaced vertically below the sled-contacting underside of first distal end projection (A222) of first knife (A212) by vertical distance (Y), such that second knife engagement surface (A346) is incapable of vertically supporting first distal end projection (A222). In response to an attempted firing stroke by the clinician, first knife (A212) advances distally while first lockout spring (A226) biases first knife (A212) downwardly against first cartridge jaw floor (A220). As shown in FIG. 19, before second sled (A338) engages any staple drivers to deploy staples from first staple cartridge (A230), middle protrusion (A218) of first knife (A212) advances downwardly into first lockout recess (A224), which inhibits further distal advancement of first knife (A212) and thus halts firing of the incompatible second staple cartridge (A330).

FIGS. 20 and 21 in combination with Table 1 below show various dimensions for first sled (A238) and second sled (A338), with a particular focus on dimensions relative to knife engagement surfaces (A246, A346), that specifically enable first and second sleds (A238, A338) to operate in the manner described above to cause a firing lockout condition and inhibit firing when first staple cartridge (A230) is mistakenly loaded by a clinician into second end effector (A300) or when second staple cartridge (A330) is mistakenly loaded by a clinician into first end effector (A200). Due to the angled planar configuration of each knife engagement surface (A246, A346), its vertical midpoint is understood to coincide with its longitudinal midpoint. Additionally, because each knife engagement surface (A246, A346) slopes downwardly in a proximal direction, it has a maximum height relative to the bottom surface of the respective sled (A238, A338) at a distal end of the knife engagement surface (A246, A346), and a minimum height relative to the bottom surface of the respective sled (A238, A338) at a proximal end of the knife engagement surface (A246, A346).

As evidenced by these dimensions, second knife engagement surface (A346) of second sled (A338) spans a vertical distance of approximately 5% of the total height of second sled (A338), or approximately 0.009 inches (0.23 mm). The vertical midpoint of second knife engagement surface (A346) is positioned at approximately 44% of a total height of second sled (A338), or approximately 0.073 inches (1.9 mm) vertically from a bottom surface of second sled (A338). The vertical midpoint of second knife engagement surface (A346) is also positioned at approximately 0.093 inches (2.4 mm) vertically from a top surface of the second sled (A338). Additionally, an upper distal end of second knife engagement surface (A346) is positioned at approximately 47% of the total sled height measured from the bottom surface of second sled (A338), and a lower proximal end of second knife engagement surface (A346) is positioned at approximately 41% of the total sled height measured vertically from the bottom surface. More specifically, the upper distal end of second knife engagement surface (A346) is positioned at approximately 0.077 inches (2.0 mm) vertically from the bottom surface of second sled (A338), and the lower proximal end of second knife engagement surface (A346) is positioned at approximately 0.068 inches (1.7 mm) vertically from the bottom surface of second sled (A338). Additionally, the vertical midpoint of the second knife engagement surface (A346) is positioned at approximately 0.036 inches (0.91 mm) vertically from an upwardly facing floor of second sled (A338).

In the case of a first version of second staple cartridge (A330) having a relatively shorter second deck (A334) for firing on relatively thicker tissues, the vertical midpoint of second knife engagement surface (A346) is positioned at approximately 34% of a total height of second staple cartridge (A330) measured vertically from the bottom surface of second pan (A336) to the top surface of second deck (A334). In the case of a second version of second staple cartridge (A330) having a relatively taller second deck (A334) for firing on relatively thinner tissues, the vertical midpoint of second knife engagement surface (A346) is positioned at approximately 30% of a total height of second staple cartridge (A330) measured vertically from the bottom surface of second pan (A336) to the top surface of second deck (A334).

It will be appreciated that similar ratios and measurements may be determined for first staple cartridge (A230) based on the dimensions provided in FIG. 20 and Table 1. For instance, the vertical midpoint of first knife engagement surface (A246) is determined to be positioned at approximately 63% of a total height of first sled (A238), or approximately 0.108 inches (2.74 mm) vertically from a bottom surface of first sled (A238).

(A410), and proximal planar underside surface (A416) extends proximally from distal planar underside surface (A414) and terminates at a relief recess (A420) formed in the body of knife (A410). Planar underside surfaces (A414, A416) are angled relative to one another, and each planar underside surface (A414, A416) is angled relative to a floor and a longitudinal jaw axis of the cartridge jaw. More specifically, proximal planar underside surface (A416) defines a first, smaller distally-opening angle relative to the cartridge jaw axis, and distal planar underside surface (A414) defines a second, larger distally-opening angle rela-

TABLE 1

| | | First Sled (A238) | | Second Sled (A338) | |
|---|---|---|---|---|---|
| Dimension | Description | in (±0.005) | mm (±0.13) | in (±0.005) | mm (±0.13) |
| A | Bottom of pan to top of deck | 0.A238 | 6.05 | 0.A238 | 6.05 |
| B | Bottom of sled to top of deck | 0.A230 | 5.84 | 0.231 | 5.87 |
| C | Top of sled to top of deck | 0.059 | 1.50 | 0.066 | 1.68 |
| D | Lower end of knife engagement surface to top of sled | 0.068 | 1.73 | 0.097 | 2.46 |
| E | Upper end of knife engagement surface to top of sled | 0.058 | 1.47 | 0.088 | 2.24 |
| F | Upper end of knife engagement surface to top of deck | 0.117 | 2.97 | 0.154 | 3.91 |
| G | Upper end of knife engagement surface to sled floor | 0.070 | 1.78 | 0.040 | 1.02 |
| H | Upper end of knife engagement surface to bottom of sled | 0.113 | 2.87 | 0.077 | 1.96 |
| I | Upper end of knife engagement surface to bottom of pan | 0.121 | 3.07 | 0.084 | 2.13 |
| J | Lower end of knife engagement surface to top of deck | 0.127 | 3.23 | 0.163 | 4.14 |
| K | Lower end of knife engagement surface to sled floor | 0.060 | 1.52 | 0.031 | 0.79 |
| L | Lower end of knife engagement surface to bottom of sled | 0.103 | 2.62 | 0.068 | 1.73 |
| M | Lower end of knife engagement surface to bottom of pan | 0.111 | 2.82 | 0.075 | 1.91 |

C. Knife Having Machined Surfaces to Optimize Engagement with Sled

Figure 22:
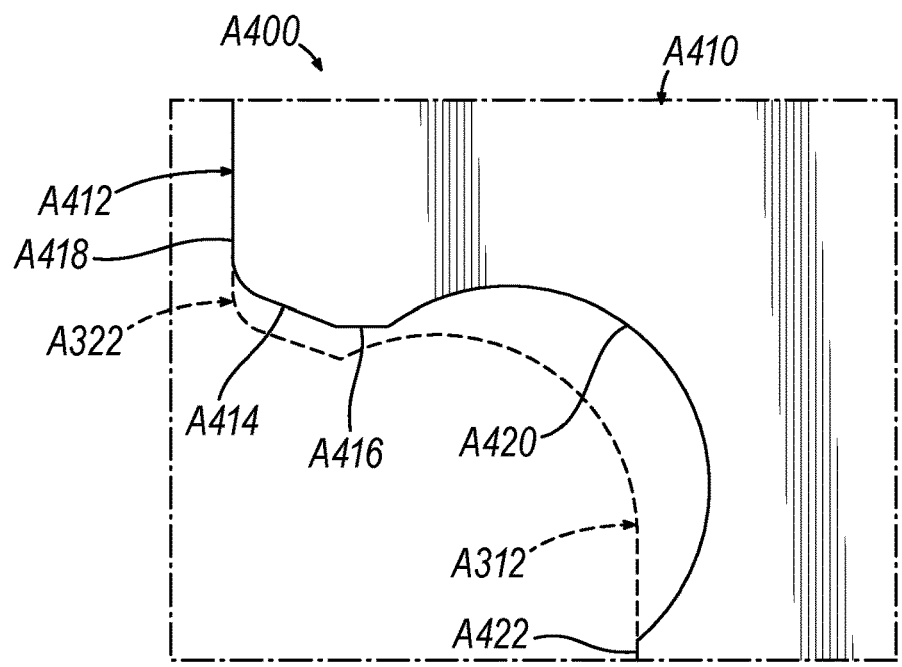
FIG. 22 depicts an enlarged side elevational view of a distal end portion of another illustrative knife in combination with a distal end portion of the knife of FIG. 16 shown in phantom.

As described above in connection with FIG. 16, the underside of second distal end projection (A322) of second knife (A312) is configured to directly contact and be vertically supported by second knife engagement surface (A346) of second sled (A338) when second end effector (A300) is fired. FIGS. 22-23C show an illustrative alternative end effector (A400) that includes a cartridge jaw (not shown) similar to cartridge jaw (A302) and configured to fully receive second staple cartridge (A330), an anvil jaw (not shown) similar to anvil jaw (A304), and a knife (A410). As described in greater detail below, knife (A410) includes a distal end projection (A412) having a geometry that slightly differs from that of second distal end projection (A322) of second knife (A312) so as to optimize an interface between its distal end projection (A412) and second knife engagement surface (A346) of second sled (A338). End effector (A400), including knife (A410), is otherwise similar in structure and function to second end effector (A300) described above.

As shown in FIG. 22, distal end projection (A412) of knife (A410) includes an underside that faces toward a floor of the cartridge jaw and includes a distal planar underside surface (A414) and a proximal planar underside surface (A416). Distal planar underside surface (A414) extends proximally from a distal-most end surface (A418) of knife tive to the cartridge jaw axis. Planar underside surfaces (A414, A416) may be formed by machining, for example.

Figure 23A:
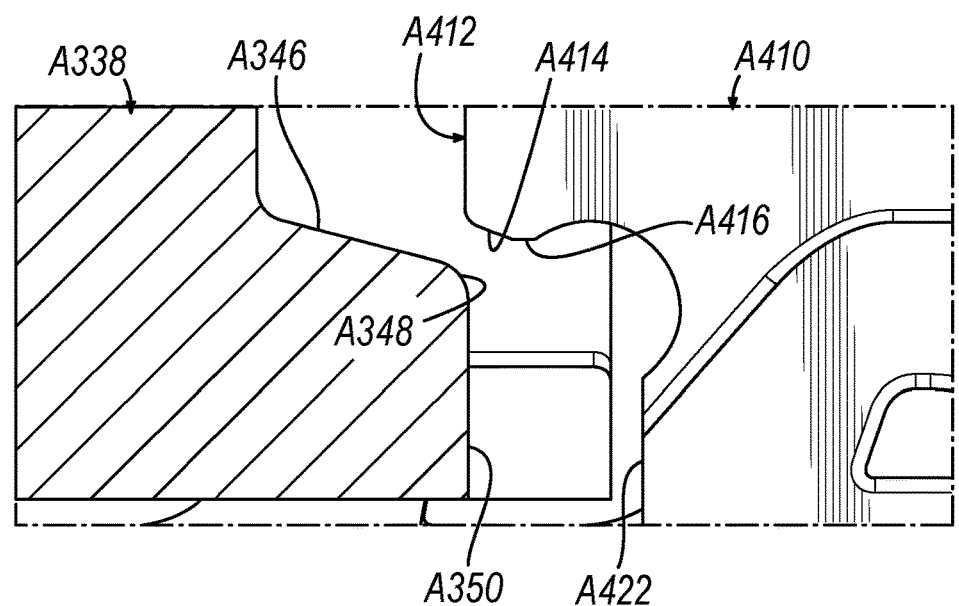
FIG. 23A depicts an enlarged side cross-sectional view of a surgical stapler end effector having the knife of FIG. 22 and properly loaded with the second staple cartridge of FIG. 11 in an unspent state, showing the knife and sled in unactuated proximal positions prior to firing.

As shown in FIG. 23A, planar underside surfaces (A414, A416) are each spaced vertically above a radiused proximal edge (A348) of second sled (A338) as knife (A410) advances distally toward second sled (A338) in its unactuated proximal position. This arrangement ensures that distal end projection (A412) does not contact radiused proximal edge (A348) and cause second sled (A338) to prematurely advance distally, which could result in knife (A410) dropping downwardly into a lockout position that inhibits firing.

Figure 23B:
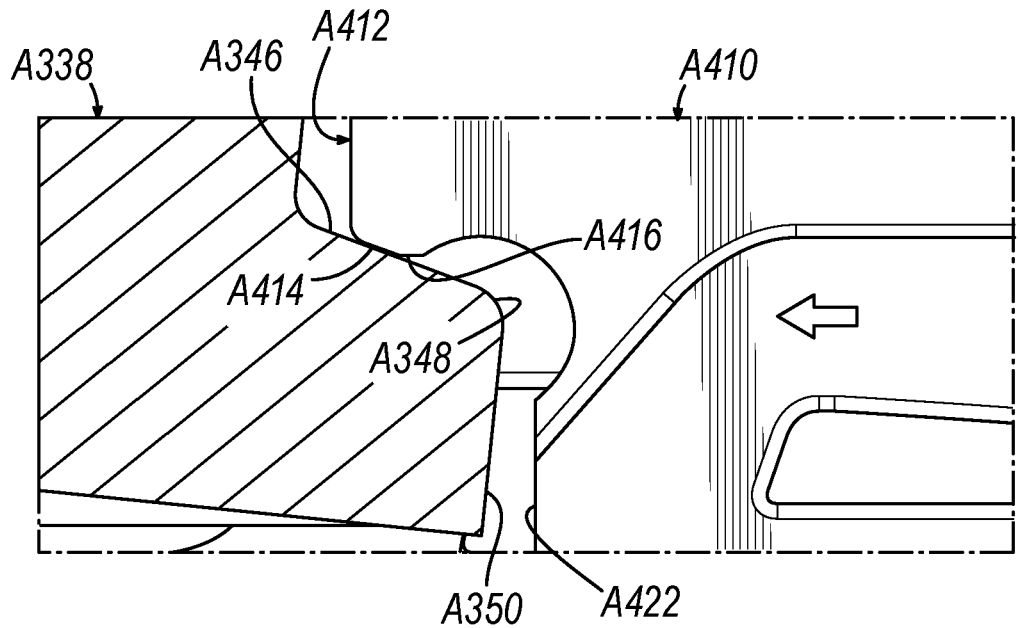
FIG. 23B depicts another enlarged side cross-sectional view of the surgical stapler end effector of FIG. 23A, showing initial engagement between the knife and the sled as the knife is advanced distally during firing.
Figure 23C:
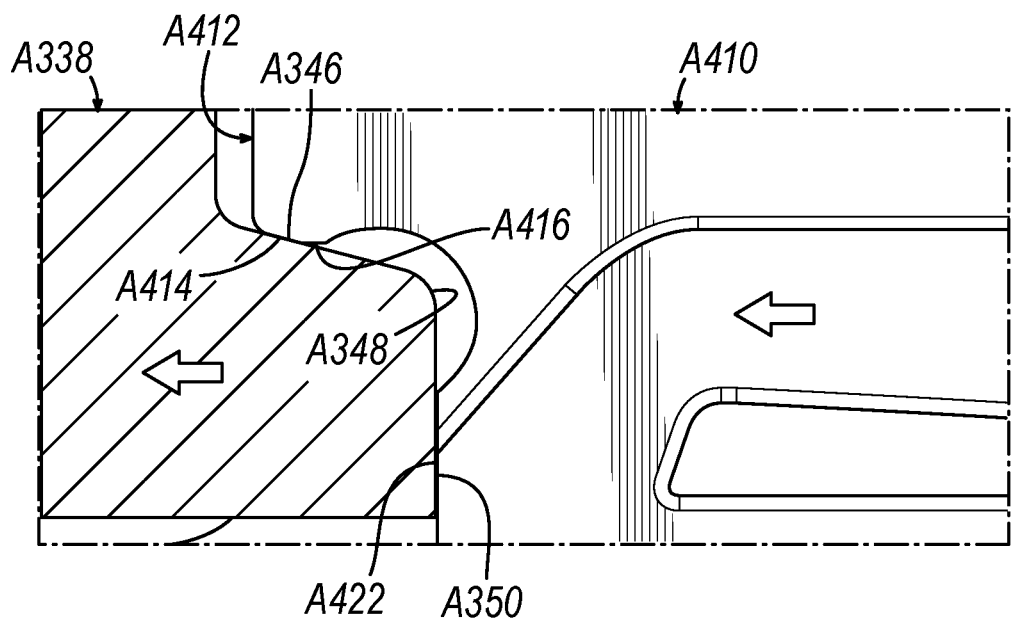
FIG. 23C depicts another enlarged side cross-sectional view of the surgical stapler end effector of FIG. 23A, showing engagement between the knife and the sled as they advance distally during a firing stroke.

As shown in FIG. 23B, upon initial engagement between knife (A410) and second sled (A338), distal end projection (A412) exerts a downward force on second knife engagement surface (A346) that may result in second sled (A338) tilting slightly proximally such that a distal end of second sled (A338) raises slightly. In this orientation, distal planar underside surface (A414) of knife (A410) maintains surface-to-surface contact with second knife engagement surface (A346), as opposed to edge-to-surface contact, which ensures that the force exerted by distal end projection (A412) on second knife engagement surface (A346) as the former distally mounts the latter is directed substantially vertically downward rather than distally. This again helps to ensure that second sled (A338) does not prematurely advance distally as knife (A410) initially engages second sled (A338), particularly in configurations where second knife engagement surface (A346) has a relatively low coefficient of friction, for example when second sled (A338) is formed of metal.

As shown in FIG. 23C, knife (A410) has been actuated further distally relative to second sled (A338) such that distal end projection (A412) has advanced further distally along second knife engagement surface (A346), and such that a distal driving surface (A422) of knife (A410) now engages a proximal end surface (A350) of second sled (A338) for firing. As knife (A410) and second sled (A338) advance distally together the distal end of second sled (A338) engages one or more initial staple drivers (not shown) of second staple cartridge (A330), which results in second sled (A338) resuming a leveled state that it maintains throughout the remainder of the distal firing stroke.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler kit, comprising: (a) a surgical stapler (10) including: (i) a body (20), (ii) a shaft (30) extending distally from the body, and (iii) an end effector (A200, A300, A400) operatively coupled with the shaft, wherein the end effector includes: (A) a cartridge jaw (A202, A302), (B) an anvil jaw (A204, A304) configured to cooperate with the cartridge jaw to clamp and staple tissue, and (C) a knife (A212, A312, A410) actuatable within the cartridge jaw and having a cutting edge (A213, A313) configured to cut tissue; (b) a first staple cartridge (A230, A330) configured to be at least partially seated within the cartridge jaw (A202, A302), wherein the first staple cartridge includes: (i) a first cartridge body (A232, A332), and (ii) a first sled (A238, A338) slidably coupled with the first cartridge body and drivable distally from a proximal undisplaced position to deploy staples from the first cartridge body; and (c) a second staple cartridge (A230, A330) configured to be at least partially seated within the cartridge jaw (A202, A302), wherein the second staple cartridge includes: (i) a second cartridge body (A232, A332), and (ii) a second sled (A238, A338) slidably coupled with the second cartridge body and drivable distally from a proximal undisplaced position to deploy staples from the second cartridge body, wherein when the first staple cartridge is at least partially seated within the cartridge jaw with the first sled in its proximal undisplaced position, the knife is configured to drive the first sled distally to deploy staples from the first cartridge body, wherein when the second staple cartridge is at least partially seated within the cartridge jaw with the second sled in its proximal undisplaced position, the knife is configured to advance distally into a lockout position before causing any staples to be deployed from the second cartridge body.

Example 2

The surgical stapler kit of Example 1, wherein a proximal end portion of each of the first staple cartridge (A230, A330) and the second staple cartridge (A230, A330) is configured to be substantially seated within the cartridge jaw (A202, A302).

Example 3

The surgical stapler kit of Example 2, wherein the proximal end portion and a distal end portion of the first staple cartridge (A230, A330) are configured to be substantially seated within the cartridge jaw (A202, A302), wherein a distal end portion of the second staple cartridge (A230, A330) is incapable of being substantially seated within the cartridge jaw.

Example 4

The surgical stapler kit of Example 3, wherein the first staple cartridge (A230, A330) includes a first lug (A240, A340) protruding laterally from a side of the first staple cartridge and the second staple cartridge (A230, A330) includes a second lug (A240, A340) protruding laterally from a side of the second staple cartridge, wherein the cartridge jaw (A204, A304) includes a sidewall (A206, A306) having a recess (A208, A308) configured to receive the first lug when the proximal end portion of the first staple cartridge is substantially seated within the cartridge jaw such that the distal end portion of the first staple cartridge is permitted to be substantially seated within the cartridge jaw, wherein the recess is incapable of receiving the second lug when the proximal end portion of the second staple cartridge is substantially seated within the cartridge jaw such that the distal end portion of the second staple cartridge is inhibited from being substantially seated within the cartridge jaw.

Example 5

The surgical stapler kit of Example 4, wherein when the proximal end portion of the second staple cartridge (A230, A330) is substantially seated within the cartridge jaw (A202, A302), at least one of: (i) the second lug (A240, A340) is longitudinally offset from the recess (A208, A308), or (ii) the second lug differs from the recess in at least one of size or shape.

Example 6

The surgical stapler kit of any of the preceding Examples, wherein a proximal end of the first sled (A238, A338) includes a first knife engagement surface (A246, A346) configured to engage and vertically support a distal end projection (A222, A322, A412) of the knife (A212, A312, A410) such that the first sled (A238, A338) in its proximal undisplaced position is configured to inhibit the knife from advancing into the lockout position, wherein the second sled (A238, A338) includes a second knife engagement surface (A246, A346) that is incapable of sufficiently vertically supporting the distal end projection of the knife such that the second sled in the proximal undisplaced position is configured to permit the knife to advance into the lockout position.

Example 7

The surgical stapler kit of Example 6, wherein the first and second knife engagement surfaces (A246, A346) face upwardly, wherein when the second staple cartridge (A230, A330) is at least partially seated within the cartridge jaw (A202, A302) a lower surface of the distal end projection (A222, A322, A412) of the knife (A212, A312, A410) is configured to remain vertically offset from the second knife engagement surface (A246, A346) to thereby permit the knife to advance downwardly into the lockout position.

Example 8

The surgical stapler kit of any of Examples 6 through 7, wherein a vertical midpoint of the first knife engagement surface (A246, A346) is positioned at a first distance from a bottom surface of the first sled (A238, A338), wherein a vertical midpoint of the second knife engagement surface (A246, A346) is positioned at a second distance from a bottom surface of the second sled (A238, A338), wherein the second distance differs from the first distance.

Example 9

The surgical stapler kit of Example 8, wherein the vertical midpoint of the first knife engagement surface (A346) is positioned at approximately 44% of a total sled height of the first sled (A338) measured vertically from the bottom surface of the first sled.

Example 10

The surgical stapler kit of Example 9, wherein the vertical midpoint of the second knife engagement surface (A246) is positioned at approximately 63% of a total sled height of the second sled (A238) measured vertically from the bottom surface of the second sled.

Example 11

The surgical stapler kit of claim of any of Examples 6 through 10, wherein the distal end projection (A412) of the knife (A410) includes a distal planar underside surface (A414) and a proximal planar underside surface (A416) that are angled relative to one another, wherein the distal planar underside surface is configured to engage the first knife engagement surface (A346) with surface-to-surface contact.

Example 12

The surgical stapler kit of any of the preceding Examples, wherein the first staple cartridge (A230, A330) has a first maximum width and the second staple cartridge (A230, A330) has a second maximum width, wherein the first and second maximum widths are substantially equal.

Example 13

The surgical stapler kit of any of the preceding Examples, wherein the surgical stapler comprises a first surgical stapler (10), the cartridge jaw comprises a first cartridge jaw (A202, A302), the anvil jaw comprises a first anvil jaw (A204, A304), and the knife comprises a first knife (A212, A312, A410), wherein the surgical stapler kit further comprises a second surgical stapler (10) having a second end effector (A200, A300, A400) that includes a second cartridge jaw (A202, A302) and a second anvil jaw (A204, A304) configured to cooperate to clamp and staple tissue, and a second knife (A212, A312, A410) actuatable within the second cartridge jaw and having a cutting edge (A213, A313) configured to cut tissue, wherein the second staple cartridge is configured to be substantially seated within the second cartridge jaw and the second knife is configured to drive the second sled (A238, A338) distally from its proximal undisplaced position to deploy staples from the second cartridge body (A232, A332) without assuming the lockout position.

Example 14

The surgical stapler kit of Example 13, wherein a proximal end portion of each of the first staple cartridge (A230, A330) and the second staple cartridge (A230, A330) is configured to be substantially seated within each of the first cartridge jaw (A202, A302) and the second cartridge jaw (A202, A302), wherein a distal end portion of the first staple cartridge is configured to be substantially seated within the first cartridge jaw but not the second cartridge jaw, wherein a distal end portion of the second staple cartridge is configured to be substantially seated within the second cartridge jaw but not the first cartridge jaw, wherein when the proximal end portion of the first staple cartridge (A230, A330) is substantially seated within the second cartridge jaw (A202, A302) with the first sled (A238, A338) in its proximal undisplaced position, the second knife (A212, A312, A410) is configured to advance distally into a lockout position before causing any staples to be deployed from the first cartridge body.

Example 15

The surgical stapler kit of any of Examples 13 through 14, wherein the first staple cartridge (A230, A330) is configured to cooperate with the first anvil jaw (A204, A304) to form staples with a first formed shape, wherein the second staple cartridge (A230, A330) is configured to cooperate with the second anvil jaw (A204, A304) to form staples with a different second formed shape, wherein one of the first formed shape or the second formed shape comprises a two-dimensional shape, wherein the other of the first formed shape or the second formed shape comprises a three-dimensional shape.

Example 16

A staple cartridge (A330) configured to be inserted into a jaw (A302) of a surgical stapler (10), comprising: (a) a cartridge body (A332) having a plurality of cartridge pockets (80) that house a plurality of staples (86); (b) a plurality of staple drivers (84) movably disposed within the staple pockets, wherein each staple driver is aligned with a respective one of the staples; and (c) a sled (A338) slidably coupled with the cartridge body, wherein the sled is drivable by a knife (A312, A410) of the surgical stapler distally along the cartridge body through a firing stroke to actuate the staple drivers and thereby drive the staples from the cartridge pockets, wherein a proximal end portion of the sled includes a knife engagement surface (A346) configured to engage and vertically support a distal end (A322, A412) of the knife during the firing stroke to thereby bypass a lockout position of the knife, wherein a vertical midpoint of the knife engagement surface is positioned at approximately 44% of a total sled height of the sled measured vertically from a bottom surface of the sled.

Example 17

The staple cartridge (A330) of Example 16, wherein the knife engagement surface (A346) is substantially planar such that the vertical midpoint coincides with a longitudinal midpoint of the knife engagement surface.

Example 18

The staple cartridge (A330) of any of Examples 16 through 17, wherein the knife engagement surface (A346) has a maximum height relative to the bottom surface of the sled (A338) at a distal end of the knife engagement surface and a minimum height relative to the bottom surface of the sled at a proximal end of the knife engagement surface.

Example 19

The staple cartridge (A330) of any of Examples 16 through 18, wherein the vertical midpoint of the knife engagement surface (A346) is positioned at approximately 0.073 inches (1.9 mm) vertically from the bottom surface of the sled (A338).

Example 20

The staple cartridge (A330) of any of Examples 16 through 19, wherein the vertical midpoint of the knife engagement surface (A346) is positioned at approximately 0.093 inches (2.4 mm) vertically from a top surface of the sled (A338).

Example 21

The staple cartridge (A330) of any of Examples 16 through 20, wherein an upper end of the knife engagement surface (A346) is positioned at approximately 47% of the total sled height measured from the bottom surface of the sled (A338), wherein a lower end of the knife engagement surface is positioned at approximately 41% of the total sled height measured vertically from the bottom surface.

Example 22

The staple cartridge (A330) of Example 21, wherein the upper end of the knife engagement surface (A346) is positioned at approximately 0.077 inches (2.0 mm) vertically from the bottom surface of the sled (A338), wherein the lower end of the knife engagement surface is positioned at approximately 0.068 inches (1.7 mm) vertically from the bottom surface of the sled.

Example 23

The staple cartridge (A330) of any of Examples 16 through 22, wherein the sled (A338) includes an upwardly facing floor opposed from the bottom surface, wherein the vertical midpoint of the knife engagement surface (A346) is positioned at approximately 0.036 inches (0.91 mm) vertically from the upwardly facing floor.

Example 24

The staple cartridge (A330) of any of Examples 16 through 23, wherein the cartridge body (A332) includes a deck surface (A334) configured to engage tissue, wherein the staple cartridge (A330) further comprises a pan (A336) positioned along an underside of the cartridge body and configured to vertically constrain the staple drivers (84) and the sled (A338) relative to the cartridge body, wherein the staple cartridge has a total cartridge height measured vertically from a bottom surface of the pan to the deck surface, wherein the vertical midpoint of the knife engagement surface (A346) is positioned at one of: (i) approximately 34% of the total cartridge height measured vertically from the bottom surface of the pan, or (ii) approximately 30% of the total cartridge height measured vertically from the bottom surface of the pan.

Example 25

The staple cartridge (A330) of any of Examples 16 through 24, wherein the knife engagement surface (A346) spans a vertical distance of approximately 5% of the total sled height of the sled (A338).

Example 26

The staple cartridge (A330) of Example 25, wherein the knife engagement surface (A346) spans a vertical distance of approximately 0.009 inches (0.23 mm).

Example 27

The staple cartridge (A330) of any of Examples 16 through 26, wherein the sled (A338) includes a central body portion (A342) and at least one fin (A344) disposed on each lateral side of the central body portion, wherein each fin includes an angled distal surface configured to cammingly engage a respective row of the staple drivers (84), wherein a proximal end of the central body portion defines the knife engagement surface (A346).

Example 28

The staple cartridge (A330) of Example 27, wherein a proximal end of the central body portion is positioned distal to a proximal end of the sled (A338).

Example 29

The staple cartridge (A330) of any of Examples 16 through 28, wherein the cartridge pockets (80) are arranged in a plurality of rows that extend linearly along the cartridge body (A332).

Example 30

The staple cartridge (A330) of any of Examples 16 through 29, wherein the staple cartridge is configured to cooperate with an anvil jaw (A304) of the surgical stapler (10) to form each of the staples (86) with a three-dimensional shape.

The following clauses also relate to various non-exhaustive ways in which the teachings herein may be combined or applied.
 1. A surgical stapler kit, comprising:
  (a) a surgical stapler including:
   (i) a body,
   (ii) a shaft extending distally from the body, and
   (iii) an end effector operatively coupled with the shaft, wherein the end effector includes:

(A) a cartridge jaw,
(B) an anvil jaw configured to cooperate with the cartridge jaw to clamp and staple tissue, and
(C) a knife actuatable within the cartridge jaw and having a cutting edge configured to cut tissue;
(b) a first staple cartridge configured to be at least partially seated within the cartridge jaw, wherein the first staple cartridge includes:
(i) a first cartridge body, and
(ii) a first sled slidably coupled with the first cartridge body and drivable distally from a proximal undisplaced position to deploy staples from the first cartridge body; and
(c) a second staple cartridge configured to be at least partially seated within the cartridge jaw, wherein the second staple cartridge includes:
(i) a second cartridge body, and
(ii) a second sled slidably coupled with the second cartridge body and drivable distally from a proximal undisplaced position to deploy staples from the second cartridge body,
wherein when the first staple cartridge is at least partially seated within the cartridge jaw with the first sled in its proximal undisplaced position, the knife is configured to drive the first sled distally to deploy staples from the first cartridge body,
wherein when the second staple cartridge is at least partially seated within the cartridge jaw with the second sled in its proximal undisplaced position, the knife is configured to advance distally into a lockout position before causing any staples to be deployed from the second cartridge body.

2. The surgical stapler kit of Clause 1, wherein a proximal end portion of each of the first staple cartridge and the second staple cartridge is configured to be substantially seated within the cartridge jaw.

3. The surgical stapler kit of Clause 2, wherein the proximal end portion and a distal end portion of the first staple cartridge are configured to be substantially seated within the cartridge jaw, wherein a distal end portion of the second staple cartridge is incapable of being substantially seated within the cartridge jaw.

4. The surgical stapler kit of Clause 3, wherein the first staple cartridge includes a first lug protruding laterally from a side of the first staple cartridge and the second staple cartridge includes a second lug protruding laterally from a side of the second staple cartridge, wherein the cartridge jaw includes a sidewall having a recess configured to receive the first lug when the proximal end portion of the first staple cartridge is substantially seated within the cartridge jaw such that the distal end portion of the first staple cartridge is permitted to be substantially seated within the cartridge jaw, wherein the recess is incapable of receiving the second lug when the proximal end portion of the second staple cartridge is substantially seated within the cartridge jaw such that the distal end portion of the second staple cartridge is inhibited from being substantially seated within the cartridge jaw.

5. The surgical stapler kit of Clause 4, wherein when the proximal end portion of the second staple cartridge is substantially seated within the cartridge jaw, at least one of:
(i) the second lug is longitudinally offset from the recess, or
(ii) the second lug differs from the recess in at least one of size or shape.

6. The surgical stapler kit of Clause 1, wherein a proximal end of the first sled includes a first knife engagement surface configured to engage and vertically support a distal end projection of the knife such that the first sled in its proximal undisplaced position is configured to inhibit the knife from advancing into the lockout position, wherein the second sled includes a second knife engagement surface that is incapable of sufficiently vertically supporting the distal end projection of the knife such that the second sled in the proximal undisplaced position is configured to permit the knife to advance into the lockout position.

7. The surgical stapler kit of Clause 6, wherein the first and second knife engagement surfaces face upwardly, wherein when the second staple cartridge is at least partially seated within the cartridge jaw a lower surface of the distal end projection of the knife is configured to remain vertically offset from the second knife engagement surface to thereby permit the knife to advance downwardly into the lockout position.

8. The surgical stapler kit of Clause 6, wherein a vertical midpoint of the first knife engagement surface is positioned at a first distance from a bottom surface of the first sled, wherein a vertical midpoint of the second knife engagement surface is positioned at a second distance from a bottom surface of the second sled, wherein the second distance differs from the first distance.

9. The surgical stapler kit of Clause 8, wherein the vertical midpoint of the first knife engagement surface is positioned at approximately 44% of a total sled height of the first sled measured vertically from the bottom surface of the first sled.

10. The surgical stapler kit of Clause 9, wherein the vertical midpoint of the second knife engagement surface is positioned at approximately 63% of a total sled height of the second sled measured vertically from the bottom surface of the second sled.

11. The surgical stapler kit of Clause 1, wherein the surgical stapler comprises a first surgical stapler, the cartridge jaw comprises a first cartridge jaw, the anvil jaw comprises a first anvil jaw, and the knife comprises a first knife, wherein the surgical stapler kit further comprises a second surgical stapler having a second end effector that includes a second cartridge jaw and a second anvil jaw configured to cooperate to clamp and staple tissue, and a second knife actuatable within the second cartridge jaw and having a cutting edge configured to cut tissue, wherein the second staple cartridge is configured to be substantially seated within the second cartridge jaw and the second knife is configured to drive the second sled distally from its proximal undisplaced position to deploy staples from the second cartridge body without assuming the lockout position.

12. The surgical stapler kit of Clause 1, wherein the first staple cartridge has a first maximum width and the second staple cartridge has a second maximum width, wherein the first and second maximum widths are substantially equal.

13. The surgical stapler kit of Clause 1, wherein the surgical stapler comprises a first surgical stapler, the cartridge jaw comprises a first cartridge jaw, the anvil jaw comprises a first anvil jaw, and the knife comprises a first knife, wherein the surgical stapler kit further comprises a second surgical stapler having a second end effector that includes a second cartridge jaw and a second anvil jaw configured to cooperate to clamp and staple tissue, and a second knife actuatable within the second cartridge jaw and having a cutting edge configured to cut tissue, wherein the second staple cartridge is configured to be substantially seated within the second cartridge jaw and the second knife is configured to drive the second sled distally from its proximal undisplaced position to deploy staples from the second cartridge body without assuming the lockout position.

14. The surgical stapler kit of Clause 13, wherein a proximal end portion of each of the first staple cartridge and the second staple cartridge is configured to be substantially seated within each of the first cartridge jaw and the second cartridge jaw, wherein a distal end portion of the first staple cartridge is configured to be substantially seated within the first cartridge jaw but not the second cartridge jaw, wherein a distal end portion of the second staple cartridge is configured to be substantially seated within the second cartridge jaw but not the first cartridge jaw, wherein when the proximal end portion of the first staple cartridge is substantially seated within the second cartridge jaw with the first sled in its proximal undisplaced position, the second knife is configured to advance distally into a lockout position before causing any staples to be deployed from the first cartridge body.

15. The surgical stapler kit of Clause 13, wherein the first staple cartridge is configured to cooperate with the first anvil jaw to form staples with a first formed shape, wherein the second staple cartridge is configured to cooperate with the second anvil jaw to form staples with a different second formed shape, wherein one of the first formed shape or the second formed shape comprises a two-dimensional shape, wherein the other of the first formed shape or the second formed shape comprises a three-dimensional shape.

16. A staple cartridge configured to be inserted into a jaw of a surgical stapler, comprising:
    (a) a cartridge body having a plurality of cartridge pockets that house a plurality of staples;
    (b) a plurality of staple drivers movably disposed within the staple pockets, wherein each staple driver is aligned with a respective one of the staples; and
    (c) a sled slidably coupled with the cartridge body, wherein the sled is drivable by a knife of the surgical stapler distally along the cartridge body through a firing stroke to actuate the staple drivers and thereby drive the staples from the cartridge pockets,
    wherein a proximal end portion of the sled includes a knife engagement surface configured to engage and vertically support a distal end of the knife during the firing stroke to thereby bypass a lockout position of the knife, wherein a vertical midpoint of the knife engagement surface is positioned at approximately 44% of a total sled height of the sled measured vertically from a bottom surface of the sled.

17. The staple cartridge of Clause 16, wherein the knife engagement surface is substantially planar such that the vertical midpoint coincides with a longitudinal midpoint of the knife engagement surface.

18. The staple cartridge of any Clause 16, wherein the knife engagement surface has a maximum height relative to the bottom surface of the sled at a distal end of the knife engagement surface and a minimum height relative to the bottom surface of the sled at a proximal end of the knife engagement surface.

19. The staple cartridge of Clause 16, wherein the vertical midpoint of the knife engagement surface is positioned at approximately 0.073 inches (1.9 mm) vertically from the bottom surface of the sled.

20. The staple cartridge of Clause 16, wherein the vertical midpoint of the knife engagement surface is positioned at approximately 0.093 inches (2.4 mm) vertically from a top surface of the sled.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/588,147, entitled "Surgical Stapler Cartridge Having Intermediate Raised Tissue Engagement Protrusions," filed on Feb. 27, 2024, published as US. Pat. Pub. No. 2024/0382197 on Nov. 21, 2024; U.S. patent application Ser. No. 18/588,175, "Surgical Stapler Cartridge Having Tissue Engagement Protrusions with Enlarged Engagement Surface," filed on Feb. 27, 2024, published as U.S. Pat. Pub. No. 2024/0382196 on Nov. 21, 2024; U.S. patent application Ser. No. 18/588,206, entitled "Surgical Stapler Cartridge Having Raised Surface to Promote Buttress Adhesion," filed on Feb. 27, 2024, published as U.S. Pat. Pub. No. 2024*/0382202 on Nov. 21, 2024; U.S. patent application Ser. No. 18/588,240, entitled "Surgical Stapler Cartridge Having Cartridge Retention Features," filed on Feb. 27, 2024, published as U.S. Pat. Pub. No. 2024/0382203 on Nov. 21, 2024; U.S. patent application Ser. No. 18/588,269, entitled "Surgical Stapler Anvil Having Staple Forming Pockets with Laterally Varying Orientations," filed on Feb. 27, 2024, published as U.S. Pat. Pub. No. 2024*/0341761 on Oct. 17, 2024; and/or U.S. patent Application Ser. No. 18/588,684, entitled "Method of Surgical Stapling," filed on Feb. 27, 2024, published as U.S. Pat. Pub. No. 2024/0350137 on Ot. 24, 2024. The disclosure of each of the above patent references is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical stapler kit, comprising:
 (a) a surgical stapler including:
  (i) a body,
  (ii) a shaft extending distally from the body, and
  (iii) an end effector operatively coupled with the shaft, wherein the end effector includes:
   (A) a cartridge jaw,
   (B) an anvil jaw configured to cooperate with the cartridge jaw to clamp and staple tissue, and
   (C) a knife actuatable within the cartridge jaw and having a cutting edge configured to cut tissue;
 (b) a first staple cartridge configured to be at least partially seated within the cartridge jaw, wherein the first staple cartridge includes:
  (i) a first cartridge body, and
  (ii) a first sled slidably coupled with the first cartridge body and drivable distally from a proximal undisplaced position to deploy staples from the first cartridge body; and
 (c) a second staple cartridge configured to be at least partially seated within the cartridge jaw, wherein the second staple cartridge includes:
  (i) a second cartridge body, and
  (ii) a second sled slidably coupled with the second cartridge body and drivable distally from a proximal undisplaced position to deploy staples from the second cartridge body,
 wherein when the first staple cartridge is at least partially seated within the cartridge jaw with the first sled in its proximal undisplaced position, the knife is configured to drive the first sled distally to deploy staples from the first cartridge body,
 wherein when the second staple cartridge is at least partially seated within the cartridge jaw with the second sled in its proximal undisplaced position, the knife is configured to advance distally into a lockout position before causing any staples to be deployed from the second cartridge body.

2. The surgical stapler kit of claim 1, wherein a proximal end portion of each of the first staple cartridge and the second staple cartridge is configured to be substantially seated within the cartridge jaw.

3. The surgical stapler kit of claim 2, wherein the proximal end portion and a distal end portion of the first staple cartridge are configured to be substantially seated within the cartridge jaw, wherein a distal end portion of the second staple cartridge is incapable of being substantially seated within the cartridge jaw.

4. The surgical stapler kit of claim 3, wherein the first staple cartridge includes a first lug protruding laterally from a side of the first staple cartridge and the second staple cartridge includes a second lug protruding laterally from a side of the second staple cartridge, wherein the cartridge jaw includes a sidewall having a recess configured to receive the first lug when the proximal end portion of the first staple cartridge is substantially seated within the cartridge jaw such that the distal end portion of the first staple cartridge is permitted to be substantially seated within the cartridge jaw, wherein the recess is incapable of receiving the second lug when the proximal end portion of the second staple cartridge is substantially seated within the cartridge jaw such that the distal end portion of the second staple cartridge is inhibited from being substantially seated within the cartridge jaw.

5. The surgical stapler kit of claim 4, wherein when the proximal end portion of the second staple cartridge is substantially seated within the cartridge jaw, at least one of:
 (i) the second lug is longitudinally offset from the recess, or
 (ii) the second lug differs from the recess in at least one of size or shape.

6. The surgical stapler kit of claim 1, wherein a proximal end of the first sled includes a first knife engagement surface configured to engage and vertically support a distal end projection of the knife such that the first sled in its proximal undisplaced position is configured to inhibit the knife from advancing into the lockout position, wherein the second sled includes a second knife engagement surface that is incapable of sufficiently vertically supporting the distal end projection of the knife such that the second sled in the proximal undisplaced position is configured to permit the knife to advance into the lockout position.

7. The surgical stapler kit of claim 6, wherein the first and second knife engagement surfaces face upwardly, wherein when the second staple cartridge is at least partially seated within the cartridge jaw a lower surface of the distal end projection of the knife is configured to remain vertically offset from the second knife engagement surface to thereby permit the knife to advance downwardly into the lockout position.

8. The surgical stapler kit of claim 6, wherein a vertical midpoint of the first knife engagement surface is positioned at a first distance from a bottom surface of the first sled, wherein a vertical midpoint of the second knife engagement surface is positioned at a second distance from a bottom surface of the second sled, wherein the second distance differs from the first distance.

9. The surgical stapler kit of claim 8, wherein the vertical midpoint of the first knife engagement surface is positioned at approximately 44% of a total sled height of the first sled measured vertically from the bottom surface of the first sled.

10. The surgical stapler kit of claim 9, wherein the vertical midpoint of the second knife engagement surface is positioned at approximately 63% of a total sled height of the second sled measured vertically from the bottom surface of the second sled.

11. The surgical stapler kit of claim 1, wherein the surgical stapler comprises a first surgical stapler, the cartridge jaw comprises a first cartridge jaw, the anvil jaw comprises a first anvil jaw, and the knife comprises a first knife, wherein the surgical stapler kit further comprises a second surgical stapler having a second end effector that includes a second cartridge jaw and a second anvil jaw configured to cooperate to clamp and staple tissue, and a second knife actuatable within the second cartridge jaw and having a cutting edge configured to cut tissue, wherein the second staple cartridge is configured to be substantially seated within the second cartridge jaw and the second knife is configured to drive the second sled distally from its proximal undisplaced position to deploy staples from the second cartridge body without assuming the lockout position.

12. The surgical stapler kit of claim 1, wherein the first staple cartridge has a first maximum width and the second staple cartridge has a second maximum width, wherein the first and second maximum widths are substantially equal.

13. The surgical stapler kit of claim 1, wherein the surgical stapler comprises a first surgical stapler, the cartridge jaw comprises a first cartridge jaw, the anvil jaw comprises a first anvil jaw, and the knife comprises a first knife, wherein the surgical stapler kit further comprises a second surgical stapler having a second end effector that includes a second cartridge jaw and a second anvil jaw configured to cooperate to clamp and staple tissue, and a second knife actuatable within the second cartridge jaw and having a cutting edge configured to cut tissue, wherein the second staple cartridge is configured to be substantially seated within the second cartridge jaw and the second knife is configured to drive the second sled distally from its proximal undisplaced position to deploy staples from the second cartridge body without assuming the lockout position.

14. The surgical stapler kit of claim 13, wherein a proximal end portion of each of the first staple cartridge and the second staple cartridge is configured to be substantially seated within each of the first cartridge jaw and the second cartridge jaw, wherein a distal end portion of the first staple cartridge is configured to be substantially seated within the first cartridge jaw but not the second cartridge jaw, wherein a distal end portion of the second staple cartridge is configured to be substantially seated within the second cartridge jaw but not the first cartridge jaw, wherein when the proximal end portion of the first staple cartridge is substantially seated within the second cartridge jaw with the first sled in its proximal undisplaced position, the second knife is configured to advance distally into a lockout position before causing any staples to be deployed from the first cartridge body.

15. The surgical stapler kit of claim 13, wherein the first staple cartridge is configured to cooperate with the first anvil jaw to form staples with a first formed shape, wherein the second staple cartridge is configured to cooperate with the second anvil jaw to form staples with a different second formed shape, wherein one of the first formed shape or the second formed shape comprises a two-dimensional shape, wherein the other of the first formed shape or the second formed shape comprises a three-dimensional shape.

16. A staple cartridge configured to be inserted into a jaw of a surgical stapler, comprising:
(a) a cartridge body having a plurality of cartridge pockets that house a plurality of staples;
(b) a plurality of staple drivers movably disposed within the staple pockets, wherein each staple driver is aligned with a respective one of the staples; and
(c) a sled slidably coupled with the cartridge body, wherein the sled is drivable by a knife of the surgical stapler distally along the cartridge body through a firing stroke to actuate the staple drivers and thereby drive the staples from the cartridge pockets,
wherein a proximal end portion of the sled includes a knife engagement surface configured to engage and vertically support a distal end of the knife during the firing stroke to thereby bypass a lockout position of the knife, wherein a vertical midpoint of the knife engagement surface is positioned at approximately 44% of a total sled height of the sled measured vertically from a bottom surface of the sled.

17. The staple cartridge of claim 16, wherein the knife engagement surface is substantially planar such that the vertical midpoint coincides with a longitudinal midpoint of the knife engagement surface.

18. The staple cartridge of any claim 16, wherein the knife engagement surface has a maximum height relative to the bottom surface of the sled at a distal end of the knife engagement surface and a minimum height relative to the bottom surface of the sled at a proximal end of the knife engagement surface.

19. The staple cartridge of claim 16, wherein the vertical midpoint of the knife engagement surface is positioned at approximately 0.073 inches (1.9 mm) vertically from the bottom surface of the sled.

20. The staple cartridge of claim 16, wherein the vertical midpoint of the knife engagement surface is positioned at approximately 0.093 inches (2.4 mm) vertically from a top surface of the sled.

* * * * *